(12) United States Patent
Emmins et al.

(10) Patent No.: US 11,098,312 B2
(45) Date of Patent: Aug. 24, 2021

(54) METHOD OF PRODUCING A RECOMBINANT PROTEIN

(71) Applicant: GlaxoSmithKline Intellectual Property Development Limited, Middlesex (GB)

(72) Inventors: Robyn Alexandra Emmins, Stevenage (GB); Gary Brian Finka, Stevenage (GB); Michael Hoare, London (GB); Alan Peter Lewis, Stevenage (GB); William John Kenneth Lewis, Stevenage (GB); Adam Daniel McInally, London (GB); Mark Uden, Stevenage (GB); Ioannis Voulgaris, London (GB)

(73) Assignee: GLAXOSMITHKLINE INTELLECTUAL PROPERTY DEVELOPMENT LIMITED, Middlesex (GB)

( * ) Notice: Subject to any disclaimer, the term of this patent is extended or adjusted under 35 U.S.C. 154(b) by 0 days.

(21) Appl. No.: 16/098,890

(22) PCT Filed: May 4, 2017

(86) PCT No.: PCT/EP2017/060654
§ 371 (c)(1),
(2) Date: Nov. 5, 2018

(87) PCT Pub. No.: WO2017/191255
PCT Pub. Date: Nov. 9, 2017

(65) Prior Publication Data
US 2019/0177734 A1 Jun. 13, 2019

Related U.S. Application Data

(60) Provisional application No. 62/332,636, filed on May 6, 2016, provisional application No. 62/338,045, filed on May 18, 2016.

(51) Int. Cl.
| | | |
|---|---|---|
| C07K 14/245 | (2006.01) | |
| C12N 15/70 | (2006.01) | |
| C12N 15/67 | (2006.01) | |
| C07K 14/705 | (2006.01) | |
| C12N 5/00 | (2006.01) | |

(52) U.S. Cl.
CPC ............ *C12N 15/70* (2013.01); *C07K 14/245* (2013.01); *C07K 14/70503* (2013.01); *C12N 5/0018* (2013.01); *C12N 15/67* (2013.01); *C07K 2319/02* (2013.01)

(58) Field of Classification Search
None
See application file for complete search history.

(56) References Cited

U.S. PATENT DOCUMENTS

2009/0011995 A1 2/2009 Lee et al.
2014/0244228 A1 8/2014 Lee et al.

FOREIGN PATENT DOCUMENTS

| RU | 2488635 | 7/2013 |
| WO | WO 2007/088371 | 8/2007 |
| WO | WO 2009/021548 A1 | 2/2009 |

OTHER PUBLICATIONS

Expasy translate results of SEQ ID No. 12 from US2014/0244228 retreived from https://web.expasy.org/translate/ on Jul. 5, 2019, 2 pages (Year: 2019).*
UNIPROT entry for ivy protein (retrieved from https://www.uniprot.org/uniprot/B7LHF1 on Dec. 6, 2019, 5 pages) (Year: 2019).*
Zhou, et al., Enhancing full-length antibody production by signal peptide engineering, *Microbial Cell Factories*, 15(1):XP055392427 (2016).
Berry et al., "Substitution of cysteine for selenocysteine in type I iodothyronine deiodinase reduces the catalytic efficiency of the protein but enhances its translation," The Endocrine Society, 1992, 131(4):1848-1852.
Frankel et al., "Characterization of diphtheria fusion proteins targeted to the human interleukin-3 receptor," Protein Engineering, 2000, 13(8):575-581.
Orlando, "Modification of proteins and low molecular weight substances with hydroxyethyl starch (HES)," GieBen, 2003, 191 pages.
Pakula et al., "Genetic analysis of protein stability and function," Annu. Rev. Genet., 1989, 23:289-310.
Chatel et al., "Ultra scale-down characterization of the impact of conditioning methods for harvested cell broths on clarification by continuous centrifugation—Recovery of domain antibodies from re coli," Biotechnol Bioeng., 2014, 111(5):913-924.
PCT International Preliminary Report on Patentability in International Appln. No. PCT/EP2017/060654, dated Nov. 6, 2018, 6 pages.
PCT International Search Report and Written Opinion in International Appln. No. PCT/EP2017/060654, dated Nov. 9, 2017, 10 pages.
Rice et al., "EMBOSS: The European Molecular Biology Open Software Suite," Trend Genet, 2000, 16(6):276-277.
Sharp et al., "The codon adaptation index—a measure of directional synonymous codon usage bias, and its potential applications," Nucleic Acids Res., 1987, 15(3):1281-1295.
Voulgaris et al., "Enhancing the selective extracellular location of a recombinant E. coli domain antibody by management of fermentation conditions," Appln. Microbial Biotechnol., 2015, 99(20):8441-8453.

* cited by examiner

*Primary Examiner* — Ronald T Niebauer
(74) *Attorney, Agent, or Firm* — Fish & Richardson P.C.

(57) ABSTRACT

The present invention relates to a recombinant signal sequence derived from *E. coli*. The invention also relates to a fusion protein comprising the signal sequence, a recombinant protein and methods of producing the recombinant protein. The recombinant signal sequence can be used to provide a method for controlling the viscosity of the fermentation, and/or controlling basal (pre-induction) expression of the recombinant protein.

19 Claims, 5 Drawing Sheets

Specification includes a Sequence Listing.

SEQUENCE LISTING

<160> NUMBER OF SEQ ID NOS: 55

<210> SEQ ID NO 1
<211> LENGTH: 8
<212> TYPE: PRT
<213> ORGANISM: Escherichia coli

<400> SEQUENCE: 1

Met Gly Arg Ile Ser Ser Gly Gly
1               5

<210> SEQ ID NO 2
<211> LENGTH: 49
<212> TYPE: DNA
<213> ORGANISM: Artificial
<220> FEATURE:
<223> OTHER INFORMATION: Synthetic sequence

<400> SEQUENCE: 2
ctctggtcat cgctaccagt gcaatggcgg aagtacaact gctggagag                49

<210> SEQ ID NO 3
<211> LENGTH: 51
<212> TYPE: DNA
<213> ORGANISM: Artificial
<220> FEATURE:
<223> OTHER INFORMATION: Synthetic sequence

<400> SEQUENCE: 3
tgatgtttaa ggcaataacg acagtcgccg ctctggtcat cgctaccagt g              51

<210> SEQ ID NO 4
<211> LENGTH: 51
<212> TYPE: DNA
<213> ORGANISM: Artificial
<220> FEATURE:
<223> OTHER INFORMATION: Synthetic sequence

<400> SEQUENCE: 4
gaccatatgg gcaggataag ctcgggagga atgatgttta aggcaataac g              51

<210> SEQ ID NO 5
<211> LENGTH: 44
<212> TYPE: DNA
<213> ORGANISM: Artificial
<220> FEATURE:
<223> OTHER INFORMATION: Synthetic sequence

<400> SEQUENCE: 5
ttctctgccg gttcagcggt tgccgaagta caactgctgg agag                     44

<210> SEQ ID NO 6
<211> LENGTH: 41
<212> TYPE: DNA
<213> ORGANISM: Artificial
<220> FEATURE:
<223> OTHER INFORMATION: Synthetic sequence

<400> SEQUENCE: 6
ggtttaacct tcgcgtccct gatgttctct gccggttcag c                        41

<210> SEQ ID NO 7
<211> LENGTH: 45
<212> TYPE: DNA
<213> ORGANISM: Artificial
<220> FEATURE:
<223> OTHER INFORMATION: Synthetic sequence

<400> SEQUENCE: 7
gaccatatga aaaaaagcct gcttggttta accttcgcgt ccctg                    45

<210> SEQ ID NO 8
<211> LENGTH: 42
<212> TYPE: DNA
<213> ORGANISM: Artificial
<220> FEATURE:
<223> OTHER INFORMATION: Synthetic sequence

<400> SEQUENCE: 8
gtgcagcgca ccggtgatgg cagaagtaca actgctggag ag                            42

<210> SEQ ID NO 9
<211> LENGTH: 42
<212> TYPE: DNA
<213> ORGANISM: Artificial
<220> FEATURE:
<223> OTHER INFORMATION: Synthetic sequence

<400> SEQUENCE: 9
cagtaatcgc agtaatggcc ctgtgcagcg caccggtgat gg                            42

<210> SEQ ID NO 10
<211> LENGTH: 47
<212> TYPE: DNA
<213> ORGANISM: Artificial
<220> FEATURE:
<223> OTHER INFORMATION: Synthetic sequence

<400> SEQUENCE: 10
gaccatatga aaaaattcgc agcagtaatc gcagtaatgg ccctgtg                       47

<210> SEQ ID NO 11
<211> LENGTH: 44
<212> TYPE: DNA
<213> ORGANISM: Artificial
<220> FEATURE:
<223> OTHER INFORMATION: Synthetic sequence

<400> SEQUENCE: 11
gtttcatcat tcagtacgca ggccgaagta caactgctgg agag                          44

<210> SEQ ID NO 12
<211> LENGTH: 47
<212> TYPE: DNA
<213> ORGANISM: Artificial
<220> FEATURE:
<223> OTHER INFORMATION: Synthetic sequence

<400> SEQUENCE: 12
ttactgttag gttcattgct tgttgtttca tcattcagta cgcaggc                       47

<210> SEQ ID NO 13
<211> LENGTH: 49
<212> TYPE: DNA
<213> ORGANISM: Artificial
<220> FEATURE:
<223> OTHER INFORMATION: Synthetic sequence

<400> SEQUENCE: 13
ttttcatcgc gcctgcgtgg ttcattactg ttaggttcat tgcttgttg                     49

<210> SEQ ID NO 14
<211> LENGTH: 44
<212> TYPE: DNA
<213> ORGANISM: Artificial
<220> FEATURE:
<223> OTHER INFORMATION: Synthetic sequence

<400> SEQUENCE: 14
gaccatatgc atttacgtca tctgttttca tcgcgcctgc gtgg        44

<210> SEQ ID NO 15
<211> LENGTH: 45
<212> TYPE: DNA
<213> ORGANISM: Artificial
<220> FEATURE:
<223> OTHER INFORMATION: Synthetic sequence

<400> SEQUENCE: 15
cctcagttct acagcggctc tggccgaagt acaactgctg gagag       45

<210> SEQ ID NO 16
<211> LENGTH: 48
<212> TYPE: DNA
<213> ORGANISM: Artificial
<220> FEATURE:
<223> OTHER INFORMATION: Synthetic sequence

<400> SEQUENCE: 16
caatcgttgt tctgtcggct ctgtccctca gttctacagc ggctctgg    48

<210> SEQ ID NO 17
<211> LENGTH: 48
<212> TYPE: DNA
<213> ORGANISM: Artificial
<220> FEATURE:
<223> OTHER INFORMATION: Synthetic sequence

<400> SEQUENCE: 17
gaccatatga aaattaaaac tctggcaatc gttgttctgt cggctctg    48

<210> SEQ ID NO 18
<211> LENGTH: 48
<212> TYPE: DNA
<213> ORGANISM: Artificial
<220> FEATURE:
<223> OTHER INFORMATION: Synthetic sequence

<400> SEQUENCE: 18
ggcagccgtg agcctgccgc tacaagcaga agtacaactg ctggagag    48

<210> SEQ ID NO 19
<211> LENGTH: 50
<212> TYPE: DNA
<213> ORGANISM: Artificial
<220> FEATURE:
<223> OTHER INFORMATION: Synthetic sequence

<400> SEQUENCE: 19
ctgggcaggt tcactggtta tgttggcagc cgtgagcctg ccgctacaag  50

<210> SEQ ID NO 20
<211> LENGTH: 45
<212> TYPE: DNA
<213> ORGANISM: Artificial
<220> FEATURE:
<223> OTHER INFORMATION: Synthetic sequence

<400> SEQUENCE: 20
gaccatatgc cactcttaaa gctctgggca ggttcactgg ttatg       45

<210> SEQ ID NO 21
<211> LENGTH: 48
<212> TYPE: DNA
<213> ORGANISM: Artificial
<220> FEATURE:
<223> OTHER INFORMATION: Synthetic sequence

<400> SEQUENCE: 21
gttttcttct gcttttatgg ctaacgccga agtacaactg ctggagag          48

<210> SEQ ID NO 22
<211> LENGTH: 53
<212> TYPE: DNA
<213> ORGANISM: Artificial
<220> FEATURE:
<223> OTHER INFORMATION: Synthetic sequence

<400> SEQUENCE: 22
acgcattgca gttgagcgtg gctgcgctgt tttcttctgc ttttatggct aac          53

<210> SEQ ID NO 23
<211> LENGTH: 48
<212> TYPE: DNA
<213> ORGANISM: Artificial
<220> FEATURE:
<223> OTHER INFORMATION: Synthetic sequence

<400> SEQUENCE: 23
gaccatatga ccattaactt ccgccgtaac gcattgcagt tgagcgtg          48

<210> SEQ ID NO 24
<211> LENGTH: 51
<212> TYPE: DNA
<213> ORGANISM: Artificial
<220> FEATURE:
<223> OTHER INFORMATION: Synthetic sequence

<400> SEQUENCE: 24
gctctggtta ttgctactag cgctatggct gaagtacaac tgctggagag c          51

<210> SEQ ID NO 25
<211> LENGTH: 52
<212> TYPE: DNA
<213> ORGANISM: Artificial
<220> FEATURE:
<223> OTHER INFORMATION: Synthetic sequence

<400> SEQUENCE: 25
atgatgttca aagcaatcac cacagtggca gctctggtta ttgctactag cg          52

<210> SEQ ID NO 26
<211> LENGTH: 55
<212> TYPE: DNA
<213> ORGANISM: Artificial
<220> FEATURE:
<223> OTHER INFORMATION: Synthetic sequence

<400> SEQUENCE: 26
gaccatatgg gacgtatttc ttcgggcgga atgatgttca aagcaatcac cacag          55

<210> SEQ ID NO 27
<211> LENGTH: 52
<212> TYPE: DNA
<213> ORGANISM: Artificial
<220> FEATURE:
<223> OTHER INFORMATION: Synthetic sequence

<400> SEQUENCE: 27
gctctggtta ttgcgacctc tgctatggca gaagtacaac tgctggagag cg         52

<210> SEQ ID NO 28
<211> LENGTH: 50
<212> TYPE: DNA
<213> ORGANISM: Artificial
<220> FEATURE:
<223> OTHER INFORMATION: Synthetic sequence

<400> SEQUENCE: 28
atgatgttca aagcaatcac taccgttgca gctctggtta ttgcgacctc             50

<210> SEQ ID NO 29
<211> LENGTH: 53
<212> TYPE: DNA
<213> ORGANISM: Artificial
<220> FEATURE:
<223> OTHER INFORMATION: Synthetic sequence

<400> SEQUENCE: 29
gaccatatgg gtcgtatctc ttccggcggt atgatgttca aagcaatcac tac         53

<210> SEQ ID NO 30
<211> LENGTH: 42
<212> TYPE: DNA
<213> ORGANISM: Artificial
<220> FEATURE:
<223> OTHER INFORMATION: Synthetic sequence

<400> SEQUENCE: 30
gaccatatga tgtttaaggc aataacgaca gtcgccgctc tg                     42

<210> SEQ ID NO 31
<211> LENGTH: 50
<212> TYPE: DNA
<213> ORGANISM: Artificial
<220> FEATURE:
<223> OTHER INFORMATION: Synthetic sequence

<400> SEQUENCE: 31
gaccatatgg gcaggataag ctcgggagga atgaagaaaa ctgctatcgc             50

<210> SEQ ID NO 32
<211> LENGTH: 36
<212> TYPE: DNA
<213> ORGANISM: Artificial
<220> FEATURE:
<223> OTHER INFORMATION: Synthetic sequence

<400> SEQUENCE: 32
cttactcgag tcattagctg cttacggtga ccagag                            36

<210> SEQ ID NO 33
<211> LENGTH: 21
<212> TYPE: PRT
<213> ORGANISM: Escherichia coli

<400> SEQUENCE: 33

Met Lys Lys Thr Ala Ile Ala Ile Ala Val Ala Leu Ala Gly Phe Ala
1               5                   10                  15

Thr Val Ala Gln Ala
            20

<210> SEQ ID NO 34
<211> LENGTH: 28
<212> TYPE: PRT
<213> ORGANISM: Escherichia coli

<400> SEQUENCE: 34

Met Gly Arg Ile Ser Ser Gly Gly Met Met Phe Lys Ala Ile Thr Thr
1               5                   10                  15
Val Ala Ala Leu Val Ile Ala Thr Ser Ala Met Ala
            20                  25

<210> SEQ ID NO 35
<211> LENGTH: 22
<212> TYPE: PRT
<213> ORGANISM: Escherichia coli

<400> SEQUENCE: 35

Met Lys Lys Ser Leu Leu Gly Leu Thr Phe Ala Ser Leu Met Phe Ser
1               5                   10                  15
Ala Gly Ser Ala Val Ala
            20

<210> SEQ ID NO 36
<211> LENGTH: 20
<212> TYPE: PRT
<213> ORGANISM: Escherichia coli

<400> SEQUENCE: 36

Met Lys Lys Phe Ala Ala Val Ile Ala Val Met Ala Leu Cys Ser Ala
1               5                   10                  15
Pro Val Met Ala
            20

<210> SEQ ID NO 37
<211> LENGTH: 30
<212> TYPE: PRT
<213> ORGANISM: Escherichia coli

<400> SEQUENCE: 37

Met His Leu Arg His Leu Phe Ser Ser Arg Leu Arg Gly Ser Leu Leu
1               5                   10                  15
Leu Gly Ser Leu Leu Val Val Ser Ser Phe Ser Thr Gln Ala
            20                  25                  30

<210> SEQ ID NO 38
<211> LENGTH: 23
<212> TYPE: PRT
<213> ORGANISM: Escherichia coli

<400> SEQUENCE: 38

Met Lys Ile Lys Thr Leu Ala Ile Val Val Leu Ser Ala Leu Ser Leu
1               5                   10                  15
Ser Ser Thr Ala Ala Leu Ala
            20

<210> SEQ ID NO 39
<211> LENGTH: 23
<212> TYPE: PRT
<213> ORGANISM: Escherichia coli

<400> SEQUENCE: 39

Met Pro Leu Leu Lys Leu Trp Ala Gly Ser Leu Val Met Leu Ala Ala
1               5                   10                  15
Val Ser Leu Pro Leu Gln Ala
            20

<210> SEQ ID NO 40
<211> LENGTH: 26
<212> TYPE: PRT
<213> ORGANISM: Escherichia coli

<400> SEQUENCE: 40

Met Thr Ile Asn Phe Arg Arg Asn Ala Leu Gln Leu Ser Val Ala Ala
1               5                   10                  15
Leu Phe Ser Ser Ala Phe Met Ala Asn Ala
            20                  25

<210> SEQ ID NO 41
<211> LENGTH: 63
<212> TYPE: DNA
<213> ORGANISM: Escherichia coli

<400> SEQUENCE: 41
atgaagaaaa ctgctatcgc tattgcggtt gctctggcag gttttgccac ggttgcgcag      60
gcc                                                                   63

<210> SEQ ID NO 42
<211> LENGTH: 84
<212> TYPE: DNA
<213> ORGANISM: Escherichia coli

<400> SEQUENCE: 42
atgggcagga taagctcggg aggaatgatg tttaaggcaa taacgacagt cgccgctctg      60
gtcatcgcta ccagtgcaat ggcg                                            84

<210> SEQ ID NO 43
<211> LENGTH: 66
<212> TYPE: DNA
<213> ORGANISM: Escherichia coli

<400> SEQUENCE: 43
atgaaaaaaa gcctgcttgg tttaaccttc gcgtccctga tgttctctgc cggttcagcg      60
gttgcc                                                                66

<210> SEQ ID NO 44
<211> LENGTH: 60
<212> TYPE: DNA
<213> ORGANISM: Escherichia coli

<400> SEQUENCE: 44
atgaaaaaat cgcagcagt aatcgcagta atggccctgt gcagcgcacc ggtgatggca      60

<210> SEQ ID NO 45
<211> LENGTH: 90
<212> TYPE: DNA
<213> ORGANISM: Escherichia coli

<400> SEQUENCE: 45
atgcatttac gtcatctgtt ttcatcgcgc ctgcgtggtt cattactgtt aggttcattg      60
cttgttgttt catcattcag tacgcaggcc                                      90

<210> SEQ ID NO 46
<211> LENGTH: 69
<212> TYPE: DNA
<213> ORGANISM: Escherichia coli

<400> SEQUENCE: 46
atgaaaatta aaactctggc aatcgttgtt ctgtcggctc tgtccctcag ttctacagcg    60
gctctggcc                                                           69

<210> SEQ ID NO 47
<211> LENGTH: 69
<212> TYPE: DNA
<213> ORGANISM: Escherichia coli

<400> SEQUENCE: 47
atgccactct aaagctctg ggcaggttca ctggttatgt tggcagccgt gagcctgccg     60
ctacaggcg                                                           69

<210> SEQ ID NO 48
<211> LENGTH: 78
<212> TYPE: DNA
<213> ORGANISM: Escherichia coli

<400> SEQUENCE: 48
atgaccatta acttccgccg taacgcattg cagttgagcg tggctgcgct gttttcttct    60
gcttttatgg ctaacgcc                                                 78

<210> SEQ ID NO 49
<211> LENGTH: 84
<212> TYPE: DNA
<213> ORGANISM: Artificial
<220> FEATURE:
<223> OTHER INFORMATION: Synthetic sequence

<400> SEQUENCE: 49
atgggacgta tttcttcggg cggaatgatg ttcaaagcaa tcaccacagt ggcagctctg    60
gttattgcta ctagcgctat ggct                                          84

<210> SEQ ID NO 50
<211> LENGTH: 84
<212> TYPE: DNA
<213> ORGANISM: Artificial
<220> FEATURE:
<223> OTHER INFORMATION: Synthetic sequence

<400> SEQUENCE: 50
atgggtcgta tctcttccgg cggtatgatg ttcaaagcaa tcactaccgt tgcagctctg    60
gttattgcga cctctgctat ggca                                          84

<210> SEQ ID NO 51
<211> LENGTH: 60
<212> TYPE: DNA
<213> ORGANISM: Artificial
<220> FEATURE:
<223> OTHER INFORMATION: Synthetic sequence

<400> SEQUENCE: 51
atgatgttta aggcaataac gacagtcgcc gctctggtca tcgctaccag tgcaatggcg    60

<210> SEQ ID NO 52
<211> LENGTH: 87
<212> TYPE: DNA
<213> ORGANISM: Artificial
<220> FEATURE:
<223> OTHER INFORMATION: Synthetic sequence

<400> SEQUENCE: 52
atgggcagga taagctcggg aggaatgaag aaaactgcta tcgctattgc ggttgctctg    60
gcaggttttg ccacggttgc gcaggcc                                       87

<210> SEQ ID NO 53
<211> LENGTH: 119
<212> TYPE: PRT
<213> ORGANISM: Artificial
<220> FEATURE:
<223> OTHER INFORMATION: Synthetic sequence

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Pro Pro Asp Gly Gln Asp Pro Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Leu Leu Pro Lys Arg Gly Pro Trp Phe Asp Tyr Trp Gly Gln Gly
            100                 105                 110

Thr Leu Val Thr Val Ser Ser
        115

<210> SEQ ID NO 54
<211> LENGTH: 357
<212> TYPE: DNA
<213> ORGANISM: Artificial
<220> FEATURE:
<223> OTHER INFORMATION: Synthetic sequence

<400> SEQUENCE: 54
gaagtacaac tgctggagag cggtggcggc ctggttcaac cgggtggttc cctgcgcctg    60
tcctgtgcgg catctggttt caccttcgca cacgaaacca tggtgtgggt tcgccaagct   120
ccgggcaaag cctggaatg gtaagccac attcctccag atggccagga cccattctat     180
gcggattccg ttaagggtcg ctttaccatt tctcgtgata actccaaaaa caccctgtac   240
ctgcagatga actccctgcg cgccgaggat actgcggtgt accattgtgc gctgctgcct   300
aaacgtggcc gtggttcga ttactggggt cagggtactc tggtcaccgt aagcagc      357

<210> SEQ ID NO 55
<211> LENGTH: 29
<212> TYPE: PRT
<213> ORGANISM: Artificial
<220> FEATURE:
<223> OTHER INFORMATION: Synthetic sequence

```
<400> SEQUENCE: 55

Met Gly Arg Ile Ser Ser Gly Gly Met Lys Lys Thr Ala Ile Ala Ile
1               5                   10                  15

Ala Val Ala Leu Ala Gly Phe Ala Thr Val Ala Gln Ala
            20                  25
```

METHOD OF PRODUCING A RECOMBINANT PROTEIN

This application is a 371 of International Application No. PCT/EP2017/060654, filed 4 May 2017, which claims priority to U.S. Provisional Application 62/332,636 filed 6 May 2016 and U.S. Provisional Application 62/338,045 filed 18 May 2016, all of which are incorporated herein in their entireties.

The present invention relates to a recombinant signal sequence, and a fusion protein comprising the signal sequence and a recombinant protein. Methods of producing the recombinant protein using the recombinant signal sequence are described. In particular, the recombinant signal sequence provides a method for controlling the viscosity of the fermentation, and/or controlling basal (pre-induction) expression of the recombinant protein.

BACKGROUND OF THE INVENTION

Large-scale and cost-effective manufacture, recovery and purification of recombinant proteins are important challenges for the biotechnology industry.

Microbial host cells are widely used organisms for the production of recombinant proteins. Considerations during production include host cell growth and expression of recombinant protein, protein titre, protein location (e.g. intracellular, extracellular, periplasmic, etc.), and selective recovery and purification from the final location of the recombinant protein. Balancing and optimising these different factors is not straightforward.

The Gram-negative *Escherichia coli* (*E. coli*) is a robust expression system for use in industrial bioprocesses due to its well-characterized genetics; its ability to accumulate biomass rapidly using inexpensive substrate; the ease of process scale-up and the large number of available host strains and expression vectors. *E. coli* is a common host for the production of therapeutic proteins do not require complex post-translational modifications such as glycosylation. For disulphide bond formation, expression can be directed into the oxidizing environment of the periplasm to facilitate correct folding. This can be achieved by the use of N-terminal signal sequences, which are recognized by components of the cell's secretion system to initiate their targeting and passage through dedicated transport systems.

Accordingly, there is a need for improved methods of producing, recovering and purifying recombinant proteins.

SUMMARY OF THE INVENTION

The present invention provides a recombinant signal sequence comprising (a) the sequence MGRISSGG (SEQ ID NO: 1) or a variant thereof that differs in sequence by 1, 2, or 3 amino acid substitutions, deletions or insertions, and (b) a heterologous signal sequence C-terminal to (a).

The invention also provides a recombinant fusion protein comprising (a) the signal sequence as defined; and (b) a heterologous recombinant protein C-terminal to (a).

The invention also provides a recombinant nucleic acid sequence which encodes the signal sequence or the fusion protein as defined.

The invention also provides a recombinant nucleic acid sequence which encodes a signal sequence comprising the sequence MGRISSGG (SEQ ID NO: 1), wherein the nucleic acid sequence has been codon optimised for expression in a host cell.

The invention also provides a recombinant expression vector comprising the nucleic acid sequence as defined.

The invention also provides a method for producing a recombinant protein in a host cell comprising:
(a) culturing the host cell under conditions that allow expression of the recombinant protein from the recombinant expression vector as defined present in the host cell; and
(b) recovering the recombinant protein.

The invention also provides a method for controlling the viscosity of a host cell broth that expresses a recombinant protein, comprising:
culturing the host cell under conditions that allow expression of the recombinant protein, wherein the host cell comprises a recombinant nucleic acid sequence which encodes (i) a recombinant signal sequence comprising the sequence MGRISSGG (SEQ ID NO: 1) or a variant thereof that differs in sequence by 1, 2, or 3 amino acid substitutions, deletions or insertions, and (ii) the recombinant protein.

The invention also provides a method for controlling basal expression of a recombinant protein expressed by a host cell broth, comprising: culturing the host cell under pre-induction conditions,
wherein the host cell comprises a recombinant nucleic acid sequence which encodes (i) a recombinant signal sequence comprising the sequence MGRISSGG (SEQ ID NO: 1) or a variant thereof that differs in sequence by 1, 2, or 3 amino acid substitutions, deletions or insertions, and (ii) the recombinant protein.

DETAILED DESCRIPTION

Figure 1:
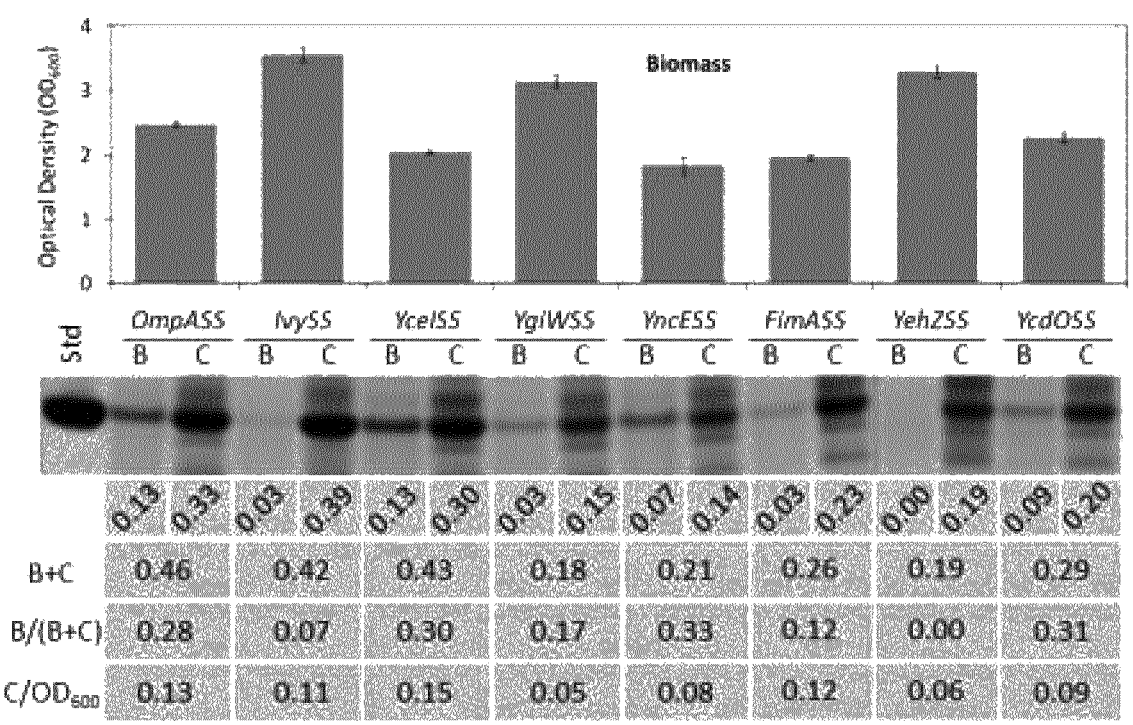
FIG. 1. The effect of different N-terminal signal sequences on the expression of dAb from *E. coli* W3110 in 24 dwp cultures. Key: B–dAb located extracellularly (supernatant); C–dAb located intracellularly (whole cell lysate: periplasmic+cytosolic). B+C–total dAb, B/(B+C)–proportion released. Summation of B and C allows visual estimation of total dAb formed. Samples were taken 24 h post-induction, reduced and bands visualised by Coomassie stained SDS-PAGE. 'Std' denotes dAb standard at 0.5 mg·mL$^{-1}$ concentration.

The present disclosure involves the realisation that the use of specific signal sequences offer advantages in terms of fermentation, recombinant protein expression, and protein recoverability.

The signal sequences have been investigated for periplasmic secretion of a recombinant protein. The signal sequences offer the advantage of a low viscosity broth, arising from a low basal expression. An eight amino acid sequence comprised in the signal sequence is identified as key to lead to this low basal expression. Codon optimisation of the signal sequences was successful in retaining low basal expression and hence low viscosity broths while increasing fermentation productivity of the recombinant protein. Hence, the combination of high productivity and practicable clarification by full-scale centrifugation is achieved.

The sequence "MGRISSGG" (SEQ ID NO: 1) can be used N-terminal (5') to any signal sequence. For example, "MGRISSGG" (SEQ ID NO: 1) may be used N-terminal to a heterologous signal sequence. A heterologous signal sequence may be one that is not the endogenous IVY signal sequence. For example, the heterologous signal sequence is a periplasmic signal sequence from E. coli. For example, the E. coli periplasmic signal sequence is OmpA, MaIE, PelB, OmpT, or LamB. For example, "MGRISSGG" (SEQ ID NO: 1) may be N-terminal to MKKTAIAIAVALAGFATVAQA (SEQ ID NO: 33), or any of the signal sequences in Table 3, or any E. coli periplasmic signal sequence.

The recombinant signal sequence comprises (a) the sequence MGRISSGG (SEQ ID NO: 1) or a variant thereof that differs in sequence by 1, 2, or 3 amino acid substitutions, deletions or insertions, and (b) a heterologous signal sequence C-terminal to (a). The heterologous signal sequence may be immediately C-terminal to MGRISSGG (SEQ ID NO: 1). For example, the recombinant signal sequence may comprise the sequence MGRISSGG (SEQ ID NO: 1) immediately N-terminal to a heterologous E. coli periplasmic signal sequence. For example, the recombinant signal sequence may comprise the sequence MGRISSGG (SEQ ID NO: 1) immediately N-terminal to the heterologous signal sequence MKKTAIAIAVALAGFATVAQA (SEQ ID NO: 33), to form recombinant signal sequence the MGRISSGGMKKTAIAIAVALAGFATVAQA (SEQ ID NO: 55).

The sequence "MGRISSGG" (SEQ ID NO: 1) may be varied by 1, 2, or 3 amino acid substitutions, deletions or insertions. The sequence "MGRISSGG" (SEQ ID NO: 1) plus a heterologous signal sequence may be varied by 1 to 10 amino acid substitutions, deletions or insertions. The variant may retain the activity of "MGRISSGG" (SEQ ID NO: 1).

The amino acid substitution may involve the replacement of at least one amino acid with an amino acid from the same class, as defined below in Table 1.

TABLE 1

| Amino acid class | Amino acid residue |
| --- | --- |
| Hydrophobic | VILMFWCGAPY |
| Uncharged polar | NQST |
| Basic polar | RKH |

The at least one amino acid substitution, deletion or insertion may preserve the primary structure of the sequence "MGRISSGG" (SEQ ID NO: 1) by maintaining a consensus sequence with: (i) one or more hydrophobic amino acid(s), (ii) one or more basic polar amino acid(s), (iii) one or more hydrophobic amino acid(s), and (iv) one or more uncharged polar amino acid(s), as defined in Table 1.

The activity of "MGRISSGG" (SEQ ID NO: 1) when N-terminal (5') to a signal sequence may be defined as the control of basal expression (pre-induction expression) of a recombinant protein. Basal expression occurs during the pre-induction exponential growth phase of the host cell. During this growth phase, the recombinant protein should not be expressed or minimised, and instead the metabolic burden of the cells is focussed on growth. However, many signal sequences allow for some basal expression of the recombinant protein. The activity of "MGRISSGG" (SEQ ID NO: 1) or a variant thereof may be to control recombinant protein basal expression to a level of 0.5 g/L or less at the time of induction, i.e. a pre-induction expression level of the recombinant protein of 0.5 g/L or less. Use of a signal sequence comprising "MGRISSGG" (SEQ ID NO: 1) can result in a low pre-induction expression level of the recombinant protein. For example, the pre-induction expression level of the recombinant protein may be ≤0.5 g/L, ≤0.4 g/L, ≤0.3 g/L, ≤0.2 g/L, ≤0.1 g/L, or ≤0.05 g/L.

Optionally in addition, the activity of "MGRISSGG" (SEQ ID NO: 1) when N-terminal (5') to a signal sequence may be defined as the control of viscosity of a host cell broth that expresses a recombinant protein. The host cell broth is comprised of the host cells plus the supernatant comprising the culture media. The broth viscosity can change during fermentation at the timepoints: pre-induction, at the point of induction, and post-induction. Use of a signal sequence comprising "MGRISSGG" (SEQ ID NO: 1) can result in a low viscosity host cell broth during fermentation. Viscosity may be measured using methods common in the field. For example, viscosity may be measured using the flow consistency index (K) or the apparent viscosity (μ).

For example, the host cell broth has a viscosity equivalent to a flow consistency index of K 0.1 Ns"m$^{-2}$ or less. For example, the host cell broth has a viscosity of K 0.05 Ns"m$^{-2}$ or less, K 0.04 Ns"m$^{-2}$ or less, K 0.03 Ns"m$^{-2}$ or less, K 0.02 Ns"m$^{-2}$ or less, or K 0.01 Ns"m$^{-2}$ or less.

For example, "low" viscosity may be equivalent to a value of K of about 0.001 Ns"m$^{-2}$ to 0.01 Ns"m$^{-2}$, "medium" viscosity may be equivalent to a value of K of about 0.01 Ns"m$^{-2}$ to 0.1 Ns"m$^{-2}$, and "high" viscosity may be equivalent to a value of K of about more than 0.1 Ns"m$^{-2}$.

Alternatively, for example, the host cell broth has an apparent viscosity µ (as defined at a shear rate of 1 s$^{-1}$) of 0.1 Nsm$^{-2}$ or less. For example, the host cell broth has an apparent viscosity of µ0.05 Nsm$^{-2}$ or less, µ0.04 Nsm$^{-2}$ or less, µ0.03 Nsm$^{-2}$ or less, µ0.02 Nsm$^{-2}$ or less, or µ0.01 Nsm$^{-2}$ or less. The apparent viscosity will vary with applied shear rate, values may be computed from values given of n the flow behaviour index and the chosen shear rate.

In one embodiment, this is the broth viscosity at the point of induction.

The nucleic acid sequence that encodes the recombinant signal sequence comprising "MGRISSGG" (SEQ ID NO: 1) may be codon optimised for expression in a host cell. Methods for codon optimisation (also known as codon adaptation) are known in the art. For example, the codon adaptation index (CAI) may be referenced against the codon usage for all genes native to a particular cell line, or for high expressing genes only. All *E. coli* genes may be referenced, or all *E. coli* K12 genes, or *E. coli* K12 class II (high expressing) genes may be referenced.

The nucleic acid sequence that encodes the signal sequence comprising "MGRISSGG" (SEQ ID NO: 1) may have a CAI score of 0.40 or above, 0.45 or above, 0.50 or above, 0.55 or above, 0.60 or above, 0.65 or above, 0.70 or above, 0.75 or above, 0.80 or above, 0.85 or above, or 0.90 or above.

For example, the nucleic acid sequence that encodes the signal sequence comprising "MGRISSGG" (SEQ ID NO: 1) may comprise the codon optimised sequence:

```
                                       (SEQ ID NO: 49)
"atgggacgtatttcttcgggcggaatgatgttcaaagcaatcaccacag
tggcagctctggttattgctactagcgctatggct";
or
                                       (SEQ ID NO: 50)
"atgggtcgtatctcttccggcggtatgatgttcaaagcaatcactaccg
ttgcagctctggttattgcgacctctgctatggca".
```

Optionally in addition, the activity of "MGRISSGG" (SEQ ID NO: 1) or a variant thereof or a codon optimised sequence, may be to control recombinant protein expression upon induction to a level of 5 g/L or more. Use of a signal sequence comprising "MGRISSGG" (SEQ ID NO: 1) can result in a high post-induction expression level of the recombinant protein. For example, the post-induction expression level of the recombinant protein may be ≥5 g/L, ≥6 g/L, ≥7 g/L, ≥8 g/L, ≥9 g/L, or ≥10 g/L. The expression level of the recombinant protein may be total produced, or extracellular protein.

Optionally in addition, the activity of "MGRISSGG" (SEQ ID NO: 1) or a variant thereof or a codon optimised sequence, may be to control recombinant protein productivity upon induction to a level of 0.1 g/L/h or more. Use of a signal sequence comprising "MGRISSGG" (SEQ ID NO: 1) can result in a high recombinant protein productivity upon induction. For example, the post-induction productivity of the recombinant protein may be ≥10 g/L/h, ≥0.11 g/L/h, ≥0.12 g/L/h, ≥0.13 g/L/h, ≥0.14 g/L/h, or ≥0.15 g/L/h. The productivity of the recombinant protein may be total produced, or extracellular protein. The time (hours) may be calculated from the point of induction.

Optionally in addition, the activity of "MGRISSGG" (SEQ ID NO: 1) or a variant thereof or a codon optimised sequence, may be to control the % solids remaining (as defined by measurement of optical density at 600 nm) after centrifugation of the harvest (i.e. clarification) to a level of 20% or less. Use of a signal sequence comprising "MGRISSGG" (SEQ ID NO: 1) can result in a low % solids remaining after centrifugation of the harvest. For example, the % solids remaining after centrifugation of the harvest may be ≤20%, ≤15%, ≤10%, ≤9%, ≤8%, ≤7%, ≤6%, or ≤5%.

Cell culture as used in the present disclosure is given its broadest meaning, namely the bulk growth of cells in a growth medium. "Fermenting" and "culturing" as used herein means bulk growing the cells in a growth medium. The terms "fermenting" and "culturing" are used interchangeably herein. The exponential phase is a period characterized by cell doubling, therefore bulk growth. The number of new cells appearing per unit time increases significantly and is proportional to the existing population. The cells may be in the exponential growth phase pre-induction. For example, basal expression of the recombinant protein is during the pre-induction exponential phase.

The stationary phase is where the growth rate and death rate of the cells is equal, leading to a linear growth phase. For example, expression of the recombinant protein is induced during the stationary phase. Cells often reach the stationary phase due to a growth-limiting factor such as the depletion of an essential nutrient, and/or the formation of an inhibitory product such as an organic acid. To maintain a constant biomass in the stationary phase and therefore bulk growth, the cells continue to grow.

Biomass can be estimated by $OD^{600}$ nm. A "high cell density" biomass may be at least $OD^{600}$ nm of 30. For example, a high cell density may refer to an $OD^{600}$ nm of at least 30, at least 40, at least 50, or at least 60. Alternatively, biomass can be measured by dry cell weight. A "high cell density" biomass may be a dry cell weight of at least 10 gL$^{-1}$. For example, a high cell density may refer to a dry cell weight of at least 10 gL$^{-1}$, at least 15 gL$^{-1}$, at least 20 gL$^{-1}$, or at least 25 gL$^{-1}$. Alternatively, biomass can be measured by wet cell weight. A "high cell density" biomass may be a wet cell weight of at least 50 gL$^{-1}$. For example, a high cell density may refer to a wet cell weight of at least 50 gL$^{-1}$, at least 70 gL$^{-1}$, at least 85 gL$^{-1}$, or at least 100 gL$^{-1}$.

The terms extracellular medium, supernatant, extracellular environment, extracellular space, culture medium, and fermentation medium, are all used herein to describe the external environment of the cells during cell culture, at the point of induction, and at the point of harvest.

The term "induction" or "inducing expression' as used herein, refers to the point at which induction of expression of the recombinant protein is initiated. For example, recombinant protein expression maybe induced by the addition of an inducer, or a change in temperature where induction is temperature dependent. The term "post-induction" is used herein to describe the elapsed time following the point at which induction is initiated.

The term "harvest" is used herein to mean the end of fermentation. Harvest may be at any time point during fermentation that is considered sufficient to end the fermentation process and recover the recombinant protein being expressed. For example, protein recovery begins at the point of harvest. The time of harvest may depend on the optimum concentration of recombinant protein in the supernatant. The recombinant protein may be recovered and purified directly from the extracellular medium of the cell culture at harvest.

Alternatively, the recombinant protein may be recovered and purified from the periplasm of the host cell.

"About" as used herein when referring to a measurable value such as an amount, a molecular weight, a temporal duration, and the like, is meant to encompass variations of ±1%, ±0.75%, ±0.5%, ±0.25%, ±0.2%, and ±0.1% from the specified value, as such variations are appropriate to perform the methods described.

Recombinant Protein

The recombinant protein may comprise an antigen binding protein, for example a monoclonal antibody, an antibody fragment, or a domain antibody (dAb).

The recombinant protein may comprise a viral protein, a bacterial toxin, a bacterial toxoid, or a cancer antigen.

As used herein a "recombinant protein" refers to any protein and/or polypeptide that can be administered to a mammal to elicit a biological or medical response of a tissue, system, animal or human. The recombinant protein may elicit more than one biological or medical response. Furthermore, the term "therapeutically effective amount" means any amount which, as compared to a corresponding subject who has not received such amount, results in, but is not limited to, healing, prevention, or amelioration of a disease, disorder, or side effect, or a decrease in the rate of advancement of a disease or disorder. The term also includes within its scope amounts effective to enhance normal physiological function as well as amounts effective to cause a physiological function in a patient which enhances or aids in the therapeutic effect of a second pharmaceutical agent.

The term "antigen binding protein" as used herein refers to antibodies, antibody fragments and other protein constructs, such as domains, which are capable of binding to an antigen.

The term "antibody" is used herein in the broadest sense to refer to molecules with an immunoglobulin-like domain. As used herein, "immunoglobulin-like domain" refers to a family of polypeptides which retain the immunoglobulin fold characteristic of antibody molecules, which contain two b-sheets and, usually, a conserved disulphide bond. This family includes monoclonal (for example IgG, IgM, IgA, IgD or IgE), recombinant, polyclonal, chimeric, humanised, bispecific and heteroconjugate antibodies; a single variable domain, a domain antibody, antigen binding fragments, immunologically effective fragments, Fab, F(ab')2, Fv, disulphide linked Fv, single chain Fv, diabodies, TANDABS™, etc.

The phrase "single variable domain" refers to an antigen binding protein variable domain (for example, VH, VHH, VL) that specifically binds an antigen or epitope independently of a different variable region or domain. A "domain antibody" or "dAb" may be considered the same as a "single variable domain".

As used herein "domain" refers to a folded protein structure which retains its tertiary structure independently of the rest of the protein. Generally, domains are responsible for discrete functional properties of proteins and in many cases may be added, removed or transferred to other proteins without loss of function of the remainder of the protein and/or of the domain. By single antibody variable domain or immunoglobulin single variable domain is meant a folded polypeptide domain comprising sequences characteristic of an antibody variable domain. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

A domain antibody can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains).

The domain antibody (dAb™) may be a human antibody variable domain. The dAb™ may be of human origin. In other words, the dAb™ may be based on a human Ig framework sequence.

As used herein, the term "antigen binding site" refers to a site on an antigen binding protein which is capable of specifically binding to an antigen, this may be a single domain, or it may be paired VH/VL domains as can be found on a standard antibody. Single-chain Fv (ScFv) domains can also provide antigen-binding sites.

The antigen binding protein may comprise additional antigen binding sites for different antigens. For example, the antigen binding protein may have specificity for more than one antigen, for example two antigens, or for three antigens, or for four antigens.

The antigen binding protein may consist of, or consist essentially of, an Fc region of an antibody, or a part thereof, linked at each end, directly or indirectly (for example, via a linker sequence) to a binding domain. Such an antigen binding protein may comprise two binding domains separated by an Fc region, or part thereof. By separated is meant that the binding domains are not directly linked to one another, and may be located at opposite ends (C and N terminus) of an Fc region, or any other scaffold region.

The antigen binding protein may comprise two scaffold regions each bound to two binding domains, for example at the N and C termini of each scaffold region, either directly or indirectly via a linker. Each binding domain may bind to a different antigen.

The antigen binding protein may take the protein scaffold format of a mAbdAb. "mAbdAb" and "dAbmAb" are used interchangeably, and are intended to have the same meaning as used herein. Such antigen-binding proteins comprise a protein scaffold, for example an Ig scaffold such as IgG, for example a monoclonal antibody, which is linked to a further binding domain, for example a domain antibody. A mAbdAb has at least two antigen binding sites, at least one of which is from a domain antibody, and at least one is from a paired VH/VL domain.

Domain antibodies can exist and bind to target in monomeric or multimeric (e.g. dimeric) forms, and can be used in combination with other molecules for formatting and targeting approaches. For example, an antigen-binding protein having multiple domains can be made in which one of the domains binds to serum proteins such as albumin. Domain antibodies that bind serum albumin (AlbudAbs) are known and can provide the domain fusion partner an extended serum half-life in its own right.

dAbs may also be conjugated to other molecules, for instance in the form of a dAb-conjugate or a dAb-fusion with other molecules e.g. a drug, another protein, an antibody molecule or an antibody fragment. For example a dAb™ can be present as a formatted dAb™, e.g. the dAb™ can be present as a dAb-Fc fusion or conjugate. Alternatively, the formatted dAb™ can be present as a mAbdAb. The dAb™ may be present as a fusion or conjugate with half life extending proteins or polypeptides, for example, a further dAb™ which binds to serum albumin (AlbudAb), or to a half life extending chemical moiety such as polyethyleneglygol (PEG). The dAb™ may be present as a fusion or conjugate with further therapeutic or active molecules.

As used herein, "drug" refers to any compound (for example, a small organic molecule, a nucleic acid, a polypeptide) that can be administered to an individual to produce a beneficial therapeutic or diagnostic effect through binding to and/or altering the function of a biological target molecule in the individual. The target molecule can be an endogenous target molecule encoded by the individual's genome (e.g., an enzyme, receptor, growth factor, cytokine encoded by the individual's genome) or an exogenous target molecule encoded by the genome of a pathogen. The drug may be a dAb™ or mAb.

A "dAb conjugate" refers to a composition comprising a dAb™ to which a drug is chemically conjugated by means of a covalent or noncovalent linkage. Preferably, the dAb™ and the drug are covalently bonded. Such covalent linkage could be through a peptide bond or other means such as via a modified side chain. The noncovalent bonding may be direct (e.g., electrostatic interaction, hydrophobic interaction) or indirect (e.g., through noncovalent binding of complementary binding partners (e.g., biotin and avidin), wherein one partner is covalently bonded to drug and the complementary binding partner is covalently bonded to the dAb™). When complementary binding partners are employed, one of the binding partners can be covalently bonded to the drug directly or through a suitable linker moiety, and the complementary binding partner can be covalently bonded to the dAb™ directly or through a suitable linker moiety.

As used herein, "dAb fusion" refers to a fusion protein that comprises a dAb™ and a polypeptide drug (which could be a polypeptide, a dAb™ or a mAb). The dAb™ and the polypeptide drug are present as discrete parts (moieties) of a single continuous polypeptide chain.

Thus the methods of the disclosure may be applied to one or more of: a therapeutic protein, a monoclonal antibody (mAb), a domain antibody (dAb™), a dAb™ conjugate, a dAb™ fusion, a mAbdAb, or any other antigen binding protein described herein.

In an embodiment, the antigen binding protein is a dAb™ which interferes with TNFα signalling. In an embodiment, the dAb™ neutralises TNFα. In an embodiment, the dAb™ specifically binds to TNFα or a TNFα receptor. In an embodiment, the dAb™ specifically binds TNFR1. In an embodiment, the antigen binding protein is VH dAb™ (anti-TNFR1)/DOM0101) of SEQ ID NO: 53 (DOM0101).

Expression of Protein: Host Cell

Suitable host cells include microbial cells such as Gram-negative bacteria for example *Escherichia coli* (e.g. W3110, and BL21), *Pseudomonas*, and *Salmonella*. In a specific embodiment the host cell is *Escherichia coli*. In an embodiment the *E. coli* strain is W3110.

A vector comprising a recombinant nucleic acid molecule encoding the signal sequence and the recombinant protein is also described herein. Such vectors are employed to genetically engineer cells to express the desired protein product. The vector may be an expression vector comprising one or more expression control elements or sequences that are operably linked to the signal sequence and the recombinant nucleic acid. Examples of vectors include plasmids and phagemids.

Suitable expression vectors can contain a number of components, for example, an origin of replication, a selectable marker gene, one or more expression control elements, such as a transcription control element (e.g. promoter, enhancer, terminator) and/or one or more translation signals, a signal sequence or leader sequence. Expression control elements and a signal sequence, if present, can be provided by the vector or other source. For example, the transcriptional and/or translational control sequences of a cloned nucleic acid encoding an antibody chain can be used to direct expression.

A promoter can be provided for expression in a desired cell. Promoters can be constitutive or inducible. For example, a promoter can be operably linked to a nucleic acid encoding an antibody, antibody chain or portion thereof, such that it directs transcription of the nucleic acid. A variety of suitable promoters for Gram negative bacteria (e.g., lac, tac, trp, phoA, lambdapL, T3, T7 (T7A1, T7A2, T7A3) promoters for *E. coli*) may be used. Operator sequences which may be employed include lac, gal, deo and gin. One or more perfect palindrome operator sequences may be employed. In an embodiment expression of the recombinant protein of the disclosure is under the control of an inducible promoter. For example, *E. coli* lac, tac, and trc promoters are inducible with lactose or the non-hydrolyzable lactose analogue, isopropyl-β-D-1-thiogalactopyranoside (IPTG) and the phoA, trp and araBAD promoters are inducible by phosphate, tryptophan and L-arabinose respectively.

In addition, expression vectors typically comprise a selectable marker for selection of cells carrying the vector, and, in the case of a replicable expression vector, an origin of replication. Genes encoding products which confer antibiotic or drug resistance are common selectable markers and may be used (e.g. lactamase gene (ampicillin resistance), Tet gene for tetracycline resistance). Dihydrofolate reductase marker genes permit selection with methotrexate in a variety of cells.

An expression vector as described in WO2007/088371 (for example pAVE037, pAVE007, or pAVE011) may be used to express the protein. In an embodiment, the vector is pAVE011. Alternatively, a vector such as pJExpress401 may be used to express the protein.

Example alternative expression vectors and methodologies (e.g. for use with CHO, PerC6 etc) are also known.

The host cell comprises the recombinant nucleic acid molecule or vector described above.

Host cell cultures of the present disclosure may be cultured in any medium that supports the host cell growth and expression of the recombinant protein. Such media are well known to those skilled in the art.

Protein Targeting

Although expression of a recombinant protein takes place in the cytoplasm, the final location of the recombinant protein may be cytoplasmic, periplasmic or extracellular depending on the nature of the recombinant protein, the host cell used and the fermentation conditions used.

The use of the signal sequences in the present invention may be with respect to a recombinant protein that is targeted to the periplasm of the cell (e.g. in Gram negative bacterium).

In Gram-negative bacteria, some secreted proteins are exported across the inner and outer membranes in a single step via the type I, type III, type IV or type VI secretion pathways, whereas other proteins are first exported into the periplasm via the universal Sec or Tat pathways and then translocated across the outer membrane mainly via the type II or type V machinery. The type II system involves a two-step process in which a premature protein containing a Sec leader sequence is exported to the periplasm using the Sec pathway. The signal sequence is removed by proteolysis resulting in a mature, processed protein being present in the periplasm and whether or not the protein is secreted to the culture medium highly depends on the characteristics of leader sequence, protein, cell and culture conditions. Also in the case of cell lysis (autolysis) it can be assumed that the majority of the protein in the culture medium originates from the periplasm and therefore is processed. The recombinant protein may be actively secreted into the culture medium via the signal sequence; or passively from the periplasm to the culture medium via other cellular pathways known in the art.

Processing of the signal sequence includes cleavage and removal of the signal sequence from the protein. However, some amino acids of the signal may remain at the N-terminus of the protein, such that the signal sequence is not properly processed. The signal sequence may be 90% or more processed, such that 10% or less of the sequence remains at the N-terminus of the protein. The signal sequence may be at least 91, 92, 93, 94, 95, 96, 97, 98, or 99% processed. The signal sequence may about 100% processed, such that none remains at the N-terminus of the protein following passage through the secretory pathway of the cell.

The signal sequence may be a periplasmic targeting signal sequence, e.g. an N-terminal periplasmic targeting sequence. Signal sequences to direct proteins to the periplasm or extracellular environment are known in the art. The signal sequence may comprise a heterologous signal sequence.

Harvest

Harvest is the end of fermentation. Harvest may be at any time point during fermentation that is considered sufficient to end the fermentation process and recover the recombinant protein being expressed. Harvest may occur between 10 and 160 hours post induction. For example, harvest may occur between 15 and 60 hours post induction. Harvest may occur 24, 48, or 55 hours post induction. At harvest, the solid content of the microbial cell population may be between 5-30% Wet Cell Weight (WCW).

The fermentor volume may be:

(i) about 10,000 litres; about 5,000 litres; about 2,000 litres; about 1,000 litres; about 500 litres; about 125 litres; about 50 litres; about 20 litres; about 10 litres; about 5 litres; or (ii) between 5 and 10,000 litres; between 10 and 5,000 litres; between 20 and 2,000 litres; between 50 and 1,000 litres.

The harvest may comprise cells that have naturally lysed, also known as auto-lysis. For example, 1-50% of the cells in the harvest may have undergone autolysis. Alternatively, 20-50%; or 30-50%; or 40-50% of the cells in the harvest have autolysed. Alternatively, 10% or more; 20% or more; 30% or more; 40% or more; or 50% or more of the cells in the harvest have autolysed. Autolysis may be indirectly determined by DNA concentration in a clarified harvest, or by capacitance.

Harvest may include the optional step of emptying the fermentor of the cells and extracellular media (i.e. the cell culture or broth).

Optional Pre-Treatment of Harvest

Dependent on host cell and recombinant protein, the pre-treatment of the harvest is a method of conditioning the harvest. This step may be carried out in the fermentor, or after the harvest has been removed from the fermentor. Pre-treatment includes: thermally, mechanically or chemically lysing the harvest (for example by homogenisation, freeze-thaw, lysis); and periplasmic extraction. At least one periplasmic extract may be extracted using methods known in the art. Alternatively if sufficient product is already present in the extracellular environment then such pre-treatment may not be required.

Clarification

Clarification is the process to remove solid particulates. Clarification can lower the burden on subsequent chromatographic steps during purification. Typical clarification steps comprise a settling step—also known as sedimentation (e.g. by gravity), and/or a centrifugation step, and/or a filtration step.

The centrifugation step may be continuous centrifugation (e.g. with a continuous feed zone). The centrifuge may in itself be operating "batch" or "intermittently" or "continuously" with respect to discharging the solids. For example, a tubular bowl centrifuge may be used as the continuous centrifugation step.

Purification of the Recombinant Protein

The recombinant protein may be recovered directly from the culture medium. Recovery of the recombinant protein is followed by purification to ensure adequate purity of the recombinant protein. One or more chromatography steps may be used in purification, for example one or more chromatography resins; and/or one or more filtration steps. For example affinity chromatography using resins such as protein A or L may be used to purify the recombinant protein. Alternatively, or in addition to, an ion-exchange resin such as a cation-exchange may be used to purify the recombinant protein.

EXAMPLES

A range of native, endogenous E. coli N-terminal signal sequences (SS) were studied for domain antibody (dAb) expression from an E. coli W3110 host strain. Two sequences with promising attributes, YceISS and IvySS were taken forward for bioreactor studies with comparison against a currently used signal sequence, OmpASS. For the bioreactor conditions studied, the use of OmpASS yielded a high product titre in a short fermentation time but with a highly viscous broth, which was predicted by ultra scale-down studies to be challenging to clarify by full-scale centrifugation. The use of YceISS led to performance comparable to that for OmpASS in terms of titre and viscosity and difficulty of centrifugation, while the use of IvySS led to a low viscosity broth which was relatively easy to centrifuge, and a high product titre but achieved over a longer fermentation time. Codon optimisation of the IvySS led to similarly low viscosity broth suitable for centrifugation and a high titre but now over shorter fermentation times comparable to that for the control using OmpASS. The improvements achieved using the IvySS or its optimised versions appear to be related to the reduced basal expression of dAb i.e. before induction. This reduced expression is believed to be due to the presence of an eight codon cassette from the N-terminus of the signal sequence, which if removed resulted in high viscosity broths similar to that obtained using the OmpASS. The relationship between basal expression and broth viscosity is investigated.

Materials and Methods

Molecular Cloning of Secretion Cassettes.

E. coli strains One Shot™ TOP10 (Life Technologies, California, USA) and W3110 (ATCC 27325) were used as a host strains for cloning and recombinant protein expression respectively. Oligonucleotides (Table 2) designed for generation of dAb secretion cassettes with various upstream signal sequences were constructed to specification (Invitrogen, Paisley, UK). Reagents used were restriction enzymes (NdeI and XhoI), T4 DNA Ligase (New England Biolabs UK Ltd., Hertfordshire, UK) and DNA polymerase (Phusion™ flash high-fidelity PCR master mix, Finnzymes Oy, Espoo, Finland). The pAVEway™ expression vector, pAVE011 (here on denoted as p11), containing the tetracycline resistance gene, tetA, and an isopropyl β-D-1-thiogalactopyranoside (IPTG) inducible T7A3 promoter (WO2007088371; Fujifilm Diosynth Biotechnologies UK Ltd., Billingham, UK) was used as a backbone for dAb secretion cassettes.

TABLE 2

Oligonucleotides used for construction of dAb gene constructs with different signal sequences. Restriction sites NdeI (CATATG) and XhoI (CTCGAG) are underlined.

| SEQ ID NO: | Oligo Name | Oligonucleotide Sequence (5' to 3') |
|---|---|---|
| 2 | IvySS fwd1 | ctctggtcatcgctaccagtgcaatggcggaagtacaactgctggagag |
| 3 | IvySS fwd2 | tgatgtttaaggcaataacgacagtcgccgctctggtcatcgctaccagtg |
| 4 | IvySS fwd3 | gaccatatgggcaggataagctcgggaggaatgatgtttaaggcaataacg |
| 5 | YceISS fwd1 | ttctctgccggttcagcggttgccgaagtacaactgctggagag |
| 6 | YceISS fwd2 | ggtttaaccttcgcgtccctgatgttctctgccggttcagc |
| 7 | YceISS fwd2 | gaccatatgaaaaaaagcctgcttggtttaaccttcgcgtccctg |
| 8 | YgiWSS fwd1 | gtgcagcgcaccggtgatggcagaagtacaactgctggagag |
| 9 | YgiWSS fwd2 | cagtaatcgcagtaatggccctgtgcagcgcaccggtgatgg |
| 10 | YgiWSS fwd3 | gaccatatgaaaaaattcgcagcagtaatcgcagtaatggccctgtg |
| 11 | YncESS fwd1 | gtttcatcattcagtacgcaggccgaagtacaactgctggagag |
| 12 | YncESS fwd2 | ttactgttaggttcattgcttgttgtttcatcattcagtacgcaggc |
| 13 | YncESS fwd3 | ttttcatcgcgcctgcgtggttcattactgttaggttcattgcttgttg |
| 14 | YncESS fwd4 | gaccatatgcatttacgtcatctgttttcatcgcgcctgcgtgg |
| 15 | FimASS fwd1 | cctcagttctacagcggctctggccgaagtacaactgctggagag |
| 16 | FimASS fwd2 | caatcgttgttctgtcggctctgtccctcagttctacagcggctctgg |
| 17 | FimASS fwd3 | gaccatatgaaaattaaaactctggcaatcgttgttctgtcggctctg |
| 18 | YehZSS fwd1 | ggcagccgtgagcctgccgctacaagcagaagtacaactgctggagag |
| 19 | YehZSS fwd2 | ctgggcaggttcactggttatgttggcagccgtgagcctgccgctacaag |
| 20 | YehZSS fwd3 | gaccatatgccactcttaaagctctgggcaggttcactggttatg |
| 21 | YcdOSS fwd1 | gttttcttctgcttttatggctaacgccgaagtacaactgctggagag |
| 22 | YcdOSS fwd2 | acgcattgcagttgagcgtggctgcgctgttttcttctgcttttatggctaac |
| 23 | YcdOSS fwd3 | gaccatatgaccattaacttccgccgtaacgcattgcagttgagcgtg |
| 24 | IvyOpt1SS fwd1 | gctctggttattgctactagcgctatggctgaagtacaactgctggagagc |
| 25 | IvyOpt1SS fwd2 | atgatgttcaaagcaatcaccacagtggcagctctggttattgctactagcg |
| 26 | IvyOpt1SS fwd3 | gaccatatgggacgtatttcttcgggcggaatgatgttcaaagcaatcaccacag |
| 27 | IvyOpt2SS fwd1 | gctctggttattgcgacctctgctatggcagaagtacaactgctggagagcg |
| 28 | IvyOpt2SS fwd2 | atgatgttcaaagcaatcactaccgttgcagctctggttattgcgacctc |
| 29 | IvyOpt2SS fwd3 | gaccatatgggtcgtatctcttccggcggtatgatgttcaaagcaatcactac |
| 30 | IvyTruncSS fwd | gaccatatgatgtttaaggcaataacgacagtcgccgctctg |
| 31 | Ivy'OmpASS fwd | gaccatatgggcaggataagctcgggaggaatgaagaaaactgctatcgc |
| 32 | dAb reverse | cttactcgagtcattagctgcttacggtgaccagag |

A selection of seven endogenous *E. coli* signal sequences (Table 3) were genetically fused upstream of a gene encoding a $V_H$ domain antibody against TNFR1 with a molecular weight of ~13.1 kDa (here on denoted as dAb, SEQ ID NO: 53). Up to four sequential PCR reactions were used to extend the upstream end of the dAb with the DNA for the desired signal sequence. This required 3 or 4 forward oligos (one for each sequential PCR reaction), reverse oligo SEQ ID NO: 32 (see Table 2) and the p11 expression plasmid as an initial template (pDAB01, see Table 3). PCR reactions contained the appropriate forward (fwd) oligo and reverse (rev) oligo SEQ ID NO: 32 (Table 2), DNA template and Phusion™ flash high-fidelity PCR master mix. Thermal cycling was performed with the following conditions: 98° C. for 10 s followed by 30 cycles of 98° C. for 1 s, 55° C. for 5 s and 72° C. for 15 s, and a final incubation at 72° C. for 1 min. After each round of PCR, the product was purified using column chromatography (QIAquick™ PCR Purification Kit, QIAGEN Ltd., Manchester, UK) and used as a DNA template for the next sequential PCR reaction until the signal sequence-dAb fusion cassette flanked by NdeI and XhoI restriction sites was generated. Secretion cassettes were digested with NdeI and XhoI and ligated into an NdeI-XhoI digested p11 expression vector using T4 DNA Ligase, then transformed by heat shock into *E. coli* One Shot™ TOP10 cells and selected on vLB agar tetracycline plates. Plasmids pDAB02 to pDAB08 (Table 3) were confirmed by DNA sequencing, then transformed into *E. coli* W3110 cells for protein expression studies. Cells banks (glycerol stocks, 20% v/v) of each prepared construct were stored at −80° C.

TABLE 3

Expression plasmids and *E. coli* signal sequenced used for dAb expression studies.
[a]Signal sequence name and [no. of codons];
[b]Signal sequences amino acid sequence with the C-terminal cleavage site at the end of the sequence.
[c]Codon adaptation index (CAI) for each signal sequence was analysed using EMBOSS suite referenced against the codon usage for *E. coli* class II (high expressing) genes (Eecoli high.cut).

| Plasmid Name | [a]Signal Sequence | [b]Amino Acid Sequence | Nucleotide Sequence (SEQ ID NO) | [c]CAI |
|---|---|---|---|---|
| pDAB01 | OmpASS [21] | MKKTAIAIAVALAGFATVAQA (SEQ ID NO: 33) | atgaagaaaactgctatcgc tattgcggttgctctggcag gttttgccacggttgcgcag gcc (SEQ ID NO: 41) | 0.701 |
| pDAB02 | IvySS [28]* | MGRISSGGMMFKAITTVAALV IATSAMA (SEQ ID NO: 34) | atgggcaggataagctcggg aggaatgatgtttaaggcaa taacgacagtcgccgctctg gtcatcgctaccagtgcaat ggcg (SEQ ID NO: 42) | 0.267 |
| pDAB03 | YceISS [22] | MKKSLLGLTFASLMFSAGSAVA (SEQ ID NO: 35) | atgaaaaaagcctgcttgg tttaaccttcgcgtccctga tgttctctgccggttcagcg gttgcc (SEQ ID NO: 43) | 0.639 |
| pDAB04 | YgiWSS [20] | MKKFAAVIAVMALCSAPVMA (SEQ ID NO: 36) | atgaaaaaattcgcagcagt aatcgcagtaatggccctgt gcagcgcaccggtgatggca (SEQ ID NO: 44) | 0.808 |
| pDAB05 | YncESS [30] | MHLRHLFSSRLRGSLLLGSLLV VSSFSTQA (SEQ ID NO: 37) | atgcatttacgtcatctgtt ttcatcgcgcctgcgtggtt cattactgttaggttcattg cttgttgtttcatcattcag tacgcaggcc (SEQ ID NO: 45) | 0.316 |
| pDAB06 | FimASS [23] | MKIKTLAIVVLSALSLSSTAALA (SEQ ID NO: 38) | atgaaaattaaaactctggc aatcgttgttctgtcggctc tgtccctcagttctacagcg gctctggcc (SEQ ID NO: 46) | 0.606 |
| pDAB07 | YehZSS [23] | MPLLKLWAGSLVMLAAVSLPLQA (SEQ ID NO: 39) | atgccactcttaaagctctg ggcaggttcactggttatgt tggcagccgtgagcctgccg ctacaggcg (SEQ ID NO: 47) | 0.377 |
| pDAB08 | YcdOSS [26] | MTINFRRNALQLSVAALFSSAFM ANA (SEQ ID NO: 40) | atgaccattaacttccgccg taacgcattgcagttgagcg tggctgcgctgttttcttct gcttttatggctaacgcc (SEQ ID NO: 48) | 0.652 |

*The amino acid sequence is as for Ivyss. The codon sequence at position 23 has been altered from gcc to gct.

TABLE 4

Expression plasmids containing modified E. coli Ivy signal sequences to investigate the effect of codon adaptation index (CAI) on the expression rate of a model dAb and subsequent effects on broth viscosity during high cell density fed-batch fermentation. [a]Signal sequence name and [no. of codons]. [b]Codon usage index for each signal sequences was analysed using EMBOSS suite referenced against the codon usage for E. coli class II (high expressing) genes (Eecoli_high.cut).

| Plasmid Name | [a]Signal Sequence | Description | Nucleotide Sequence | [b]CAI |
|---|---|---|---|---|
| pDAB021 | IvyOpt1SS [28] | Full codon optimisation with reference to E. coli genes | Atgggacgtatttcttcgggcggaatgatgttcaaa gcaatcaccacagtggcagctctggttattgctact agcgctatggct (SEQ ID NO: 49) | 0.580 |
| pDAB022 | IvyOpt2SS [28] | Full codon optimisation with reference to class II genes only | atgggtcgtatctcttccggcggtatgatgttcaaa gcaatcactaccgttgcagctctggttattgcgacc tctgctatggca (SEQ ID NO: 50) | 0.899 |
| pDAB023 | IvyTruncSS [20] | First 8 IvySS codons removed | atgatgtttaaggcaataacgacagtcgccgctctg gtcatcgctaccagtgcaatggcg (SEQ ID NO: 51) | 0.403 |
| pDAB011 | Ivy'OmpASS [29] | First 8 IvySS codons + OmpASS MGRISSGGMKKTAIAIAVALAGFA TVAQA (SEQ ID NO: 55) | atgggcaggataagctcgggaggaatgaagaaaact gctatcgctattgcggttgctctggcaggttttgcc acggttgcgcaggcc (SEQ ID NO: 52) | 0.396 |

TABLE 5

Effect of N-terminal signal peptide sequence on the level of basal dAb expression, broth viscosity and initial productivity during high cell density E. coli fermentation.

| | Signal sequences [CAI, No. of codons, CAI/No.] | | |
|---|---|---|---|
| | No Cassette OmpASS [0.702, 21, 0.033] | [b] Cassette | |
| Output | YcelSS [0.639, 21, 0.029] IvyTruncSS [0.403, 20, 0.020] | IvySS [0.267, 28, 0.009] Ivy'OmpASS [0.396, 29, 0.013] | IvyOpt1SS [0.580, 28, 0.021] IvyOpt2SS [0.899, 28, 0.032] |
| Basal Expression | High | Low | Low |
| Viscosity (Pre-Induction) | High | Low | Low |
| [a] Initial Productivity | High | Low | High |

[a] Initial productivity is the total dAb expressed in the first 24 h post-induction (FIGS. 2E & 4E).
[b] The N-terminal cassette comprises the codons for the first eight amino acids from the IvySS.

Secretion cassettes for dAb expression plasmids pDAB021 and pDAB022 (Table 4) containing codon optimised Ivy signal sequences, IvyOpt1SS and IvyOpt2SS, were generated by PCR amplification of the gene coding for dAb from pDAB01 (as described above) using fwd oligos 23-25 and 26-28 respectively and reverse oligo SEQ ID NO: 32 (Table 2). The secretion cassette for pDAB023 (Table 4) containing a truncated Ivy signal sequence (IvyTruncSS) upstream of dAb was generated by PCR amplification using pDAB02 as a template (Table 3) and fwd oligo 29 and rev oligo 31. The secretion cassette for pDAB011 encoded for the dAb with the upstream signal sequence Ivy'OmpASS composed of the first 8 codons of the IvySS fused to OmpASS. This was generated by amplifying the gene encoding the OmpASS-dAb from pDAB01 (Table 3) using fwd oligo 30 and rev oligo SEQ ID NO: 32. All secretion cassettes were subsequently ligated into the p11 vector at NdeI/XhoI and transformed into the E. coli W3110 strain.

The codon adaptation index (CAI) (Sharp and Li 1987) for each signal sequence was determined using EMBOSS suite (Rice et al. 2000) referenced against the codon usage for class II (high expressing) genes only (Eecoli_high.cut). IvySS was codon optimised for expression in E. coli using a codon adaptation algorithm (Leto Software, version 1.0.26, Entelechon GmbH, Regensburg, Germany). The codon (Leto) threshold was set at 70% with reference to all E. coli K12 genes and also for E. coli K12 class II (high expressing) genes only to generate IvyOpt1SS and IvyOpt2SS respectively (Table 4).

Fermentation.

All media and reagents were purchased from Sigma-Aldrich (Dorset, UK) unless specified. Inoculum and 24-deep well plate (24 dwp) cultivation was performed in Luria Bertani (vLB) media (pH 7.0): 10 g·L$^{-1}$ Difco™ Select Soytone (Becton Dickinson and Co. (BD), New Jersey, USA), 5 g·L$^{-1}$ Bacto™ Yeast Extract (BD) and 5 g·L$^{-1}$ NaCl. 10× concentrated glycerol boost (pH 7.0) for 24 dwp cultures contained: 70 g·L$^{-1}$ glycerol, 50 g·L$^{-1}$ Yeast Extract (BD), 25 g·L$^{-1}$ $(NH_4)_2SO_4$ and 1.0 µg·mL$^{-1}$ thiamine. High cell density fermentation was performed in a complex medium as described elsewhere (Voulgaris et al. 2015). All fermentation media (excluding TB/SB feed) was supplemented with 15 µg·mL$^{-1}$ tetracycline (Tet) for selectivity of E. coli clone containing the p11 expression plasmid.

For deep well plate expression inoculum cultures in vLB media (20 mL) were prepared in 125 mL Erlenmeyer, baffled, vent cap shake flasks (Corning Life Sciences, Amsterdam, Netherlands) with 0.5% v/v E. coli W3110 transformed with a pDAB expression plasmid. Cultures were incubated overnight at 23° C., 230 rpm in an orbital shaker with a 25 mm offset (Climo-shaker ISF1-X, Kühner Shaker Ltd., Derbyshire, UK) to an $OD_{600\ nm}$ of 1-2. This was used to inoculate fresh vLB media to an $OD_{600\ nm}$ of 0.05 and was dispensed into pyramid bottom square shaped wells (2 mL working volume) of 24-deep well microtitre plates (24 dwp; Porvair Sciences Ltd., Wrexham, UK) and covered with a high cell density gas-permeable lid system (Applikon Biotechnology, Tewkesbury, UK). Plates were incubated at 37° C., 230 rpm to $OD_{600\ nm}$ 0.7-1.0 and then dAb formation was induced with 0.1 mM IPTG with simultaneous addition of 10× glycerol boost (see above for recipe). Cultures were incubated for a further 24 h at 23° C., 230 rpm. Harvest cultures (2 mL) were pelleted (16100×g for 10 min) and the broth supernatant extracted. Pellets were resuspended in 1 mL 0.1 M PBS and centrifuged again as before. Broth supernatant and pellets were stored at −20° C.

For Bioreactor expression inoculum cultures in vLB media (200 mL) were prepared with 0.5% v/v glycerol stocks in 500 mL Erlenmeyer, baffled, vent cap shake flasks (Corning Life Sciences). Cultures were incubated at 37° C., 230 rpm in an orbital shaker for 4-5 h until an $OD_{600\ nm}$ of 1-2 and used at 0.05% v/v to inoculate a 1 L working volume reactor (SR1000DLL bioreactor, vessel dia 100 mm, aspect ratio 2.4:1, overhead driven triple Rushton 6-blade, 46 mm dia, impellers, DASGIP AG, Jülich, Germany) containing the complex medium mentioned above. The reactor was maintained at: 30° C., pH 7.0±0.05 (using 25% v/v $H_3PO_4$ and 30% v/v $NH_4OH$); Dissolved Oxygen (DO) 30±5% (by cascade control using: (1) impeller speed (400-1200 rpm); (2) gas flow rate (1-2 vvm) and (3) oxygen content (21-100%)). Feed medium was automatically added at 6.0 $mL \cdot L^{-1} \cdot h^{-1}$ starting 10 min after the DO spike indicating complete glycerol consumption. Production of dAb was induced with the addition of 0.2 mM IPTG once the culture had reached an $OD_{600\ nm}$ of 75±3 (corresponding to a biomass of approximately 25 dcw $g \cdot L^{-1}$) and the feed rate was reduced to 3.6 $mL \cdot L^{-1} \cdot h^{-1}$ for the rest of the fermentation. Real-time values of pH, dissolved oxygen, agitation speed, temperature, air-flow rate, oxygen percentage, oxygen uptake rate, carbon dioxide evolution rate were recorded (DASGIP Control, Jülich, Germany). The rheological characteristic of the fresh cell broth was measured (DV-II+ Programmable Viscometer fitted with either ULA, 1.233N or SSA, 1.32N spindle, Brookfield Engineering Laboratories Inc., Massachusetts, USA) over increasing and decreasing shear sweeps (1.3 to 110 $s^{-1}$ in five increments with 30 s hold at each increment) at 25° C. Rheology is used as an indication of broth processability e.g. by centrifugation.

Cell Broth Processing.

An ultra scale-down shear device (20 mL stainless steel chamber, 50 mm dia×10 mm height, fitted with a stainless steel rotating disc, 40 mm dia×0.1 mm thick, 12000 rpm, constructed in the UCL mechanical workshop) was used to expose cell broth samples to a maximum energy dissipation rate (ε) of $0.53 \times 10^6$ $W \cdot kg^{-1}$ for 20 s (Chatel et al. 2014a). Such an ε value typically mimics that which occurs in the feed zone of a high shear continues-flow industrial scale centrifuge. Samples (2 mL of sheared or non-sheared broth) were then centrifuged (3400×g for 7 min at 21° C., Centrifuge 5415R, Eppendorf, Cambridge, UK) and the supernatants (0.8 mL) were recovered. These were characterized in terms of the solids remaining by measurement at $OD_{600\ nm}$ corrected against a baseline $OD_{600\ nm}$ value for a well-clarified sample (16100×g for 30 min). The centrifugation conditions were characterized in terms of the group V/tΣ, where V is volume centrifuged (2.0 mL), t is time of centrifugation (420 s) and Σ is equivalent settling area of the centrifuge tube for the particular rotational speed and geometry of centrifuge head (=0.164 $m^2$—see Chatel et al. 2014a for details of calculation).

Analytical Methods.

Cell pellets were thawed and resuspended in 1 mL (24 dwp samples) or 4 mL (1 L bioreactor samples) of 50 mM Tris-HCl pH 7.5. 1 mL of each resuspended pellet was lysed (Soniprep 150 Plus Ultrasonic disintegrator fitted with an exponential microprobe, part no. 38121-114A, MSE (UK) Ltd., London, UK) using two pulses of 30 s on and 10 s off at amplitude 8.0. The lysed whole cell sample was then centrifuged at 16100×g for 20 min and the supernatant recovered. Fermentation broth samples and whole cell lysates were then filtered using a 0.22 μm filter plate centrifuged at 3000×g for 30 min (GHP membrane, AcroPrep™ 96 Filter Plate, Pall Life Sciences, Portsmouth, UK). The expression of dAb from E. coli 24 dwp cultures was analysed by SDS-PAGE. Samples were reduced, denatured and loaded on a SDS-PAGE gel (NuPAGE® 4-12% Bis-Tris, Invitrogen) with gel electrophoresis performed in 1× MES running buffer (Invitrogen) as per the manufacturer's instructions. Protein was detected by Coomassie staining and product was quantified using densitometry software (Image Lab version 3.0, Bio-Rad Laboratories). For high cell density E. coli fermentation, dAb product titre in the broth supernatant and whole cell lysate were determined by Protein A HPLC (HP1100 with a chilled autosampler, Agilent Technologies UK Limited, Cheshire, UK) fitted with a 1 mL HiTrap MabSelect Xtra column (GE Healthcare Life Science, Buckinghamshire, UK). The column was equilibrated and washed with 0.1 M PBS pH 7.3 and 20 mM HCl pH 1.8 was used for product elution (protein concentration was monitored at 280 nm). Concentration of dAb was determined using a standard curve. The molecular weight of the purified dAb was determined using liquid chromatography time-of-flight mass spectrometry (GSK in-house method using Agilent HP1100, Agilent Technologies UK Ltd., coupled to a Micromass LCT mass spectrometer, Waters, Mass., USA, equipped with an electrospray ionization (ESI) probe and was controlled using MassLynx, version 4.1, Waters, software). Double-stranded DNA was measured using fluorometry (Qubit™ dsDNA BR Assay kit, Life Technologies) as per the manufacturer's instructions.

Example 1

FIG. 1 shows the final biomass levels and SDS-PAGE gels, detailing the expression of dAb in terms of extracellular and intracellular location, of an initial screen of N-terminal signal sequences.

The effect of different N-terminal signal sequences on the expression of dAb from E. coli W3110 in 24 dwp fermentations is shown in FIG. 1. Key: B–dAb located extracellularly (supernatant); C–dAb located intracellularly (whole cell lysate: periplasmic+cytosolic). B+C–total dAb, B/(B+C)–proportion released. Summation of B and C allows visual estimation of total dAb formed. Samples were taken 24 h post-induction, reduced and bands visualised by Coomassie stained SDS-PAGE. 'Std' denotes dAb standard at 0.5 $mg \cdot mL^{-1}$ concentration.

The use of the OmpA signal sequence (OmpASS), IvySS and YceISS results in high dAb expression levels per unit volume of broth (broth=cells+supernatant, i.e. extracellular medium), while the use of YgiWSS, YncESS, FimASS, YehZSS and YcdOSS signal sequences gives moderate expression levels. OmpASS, IvySS, YceISS and FimASS result in high intracellular product levels per unit $OD_{600\ nm}$, while YgiWSS, YncESS, YehZSS and YcdOSS result in moderate levels. There is some positive correlation between the intracellular product level per unit $OD_{600\ nm}$ and product release to the supernatant for OmpASS, YceISS, YgiWSS, FimASS, and YehZSS. The use of YceISS, YncESS and YcdOSS appears to lead to high release levels and for YceISS, this plus the high titre achieved, makes it one candidate for further study. IvySS exhibits a relatively low release to the supernatant and a high $OD_{600\ nm}$, which might signify further potential for dAb formation. This plus the resulting high total product and relatively low proportional release of dAb to broth identifies it as the second candidate for further study. These two strains are carried forward for more detailed study of growth in bioreactors against the use of OmpASS as a control.

Example 2

Figure 2:
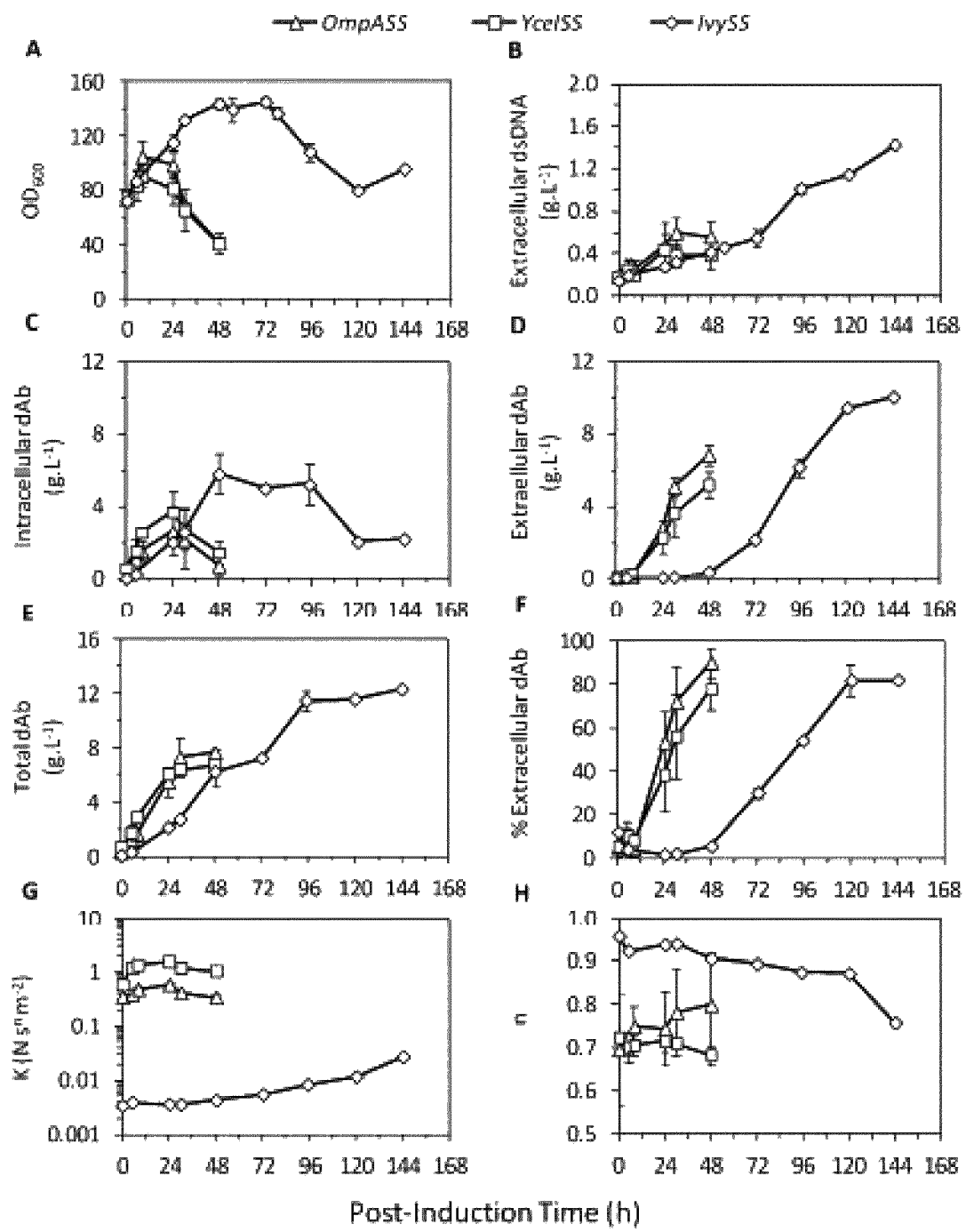
FIG. 2. Post-induction fermentation profiles for high cell density *E. coli* W3110 fed-batch cultures. N-terminal signal sequence and basal (pre-induction) expression level: (Δ), OmpASS, 0.30 g·L$^{-1}$, (□) YceISS, 0.64 g·L$^{-1}$ or (◊), IvySS, 0.061 g·L$^{-1}$. All results are taken post-induction of dAb formation with IPTG. (A) Biomass was estimated by OD$_{600\ nm}$; (B) Extracellular soluble dsDNA concentration; dAb yield was determined (C) intracellularly (whole cell lysate), (D) extracellularly (supernatant), as (E) total dAb formed (intracellular+extracellular) and as (F) percentage of total dAb in the extracellular space. Broth viscosity, μ, is described in terms of a power law relationship, $\mu=K\gamma^{n-1}$ where γ is shear rate, (G) K is the flow consistency index, and (H) n is the flow behaviour index. Results were taken from replicated fermenters (n=2–4) averaged and error bars added corresponding to one standard deviation.

The effect of using OmpASS, YceISS and IvySS on the fed-batch fermentation of *E. coli* W3110 is described in FIG. 2. The fermentation was monitored in the post-induction phase via $OD_{600\,nm}$ as an indication of cell growth, dsDNA release as an indication of lysis, extracellular and intracellular dAb as an indication of productivity and product location, rheology as an indication of broth processability e.g. by centrifugation.

FIG. 2 shows post-induction fermentation profiles for high cell density *E. coli* W3110 fed-batch cultures. N-terminal signal sequence and basal (pre-induction) expression level: (Δ), OmpASS, 0.30 g·L$^{-1}$, (☐) YceISS, 0.64 g·L$^{-1}$ or (◇), IvySS, 0.061 g·L$^{-1}$. All results are taken post-induction of dAb formation with IPTG. (A) Biomass was estimated by $OD_{600\,nm}$; (B) Extracellular soluble dsDNA concentration; dAb yield was determined (C) intracellularly (whole cell lysate), (D) extracellularly (supernatant), as (E) total dAb formed (intracellular+extracellular) and as (F) percentage of total dAb in the extracellular space. Broth viscosity, µ, is described in terms of a power law relationship, $\mu=K\gamma^{n-1}$ where γ is shear rate, (G) K is the flow consistency index, and (H) n is the flow behaviour index. Results were taken from replicated fermenters (n=2-4) averaged and error bars added corresponding to one standard deviation.

TABLE 6

| Signal sequence | dAb pre-induction basal expression, g · L$^{-1}$ (+/−sd or range) |
|---|---|
| OmpASS | 0.30 ± 0.15 |
| YceISS | 0.64 ± 0.06 |
| IvySS | 0.061 ± 0.006 |

The strain using the OmpASS (Δ), demonstrated a typical phase of rapid growth followed by cell autolysis as evidenced by a simultaneous decrease in $OD_{600\,nm}$ (FIG. 2A) and increase in extracellular dsDNA (FIG. 2B). This coincided with rapid formation of dAb with release into the extracellular environment/supernatant (FIGS. 2C & D). The total dAb formed is summarised in FIG. 2E, with nearly all occurring extracellularly by the end of the fermentation (FIG. 2F). At the point of induction a significant amount (0.30 g·L$^{-1}$) of dAb had been already expressed in the cells (FIG. 2C & legend). This was accompanied by the formation of a highly viscous, shear thinning broth by the start of the induction phase (FIGS. 2G & H). The broth viscosity continued to increase for 24 h during the post-induction phase (FIG. 2G) with a parallel increase in extracellular dsDNA levels.

Similar trends to the use of OmpASS culture are observed for the use of YceISS (☐). Here the product expression level at induction (0.64 g·L$^{-1}$) is greater than for strains using OmpASS. This is accompanied by a greater broth viscosity at induction and subsequently, reduced cell growth and slightly lower product levels either as total or as extracellular dAb.

In contrast, the use of IvySS (◇) led to low dAb expression levels of 0.061 g·L$^{-1}$ at the time of induction and a low viscosity broth. This is followed by a viscosity increase throughout the fermentation progression in parallel with an increased dsDNA release (FIG. 2B). Cell growth continues for a longer period before the onset of lysis at ~72 h i.e. compared with ~12 h observed for the use of OmpASS and YceISS. The resultant effect is a slower rate of dAb expression and delayed release of dAb to the extracellular space (FIGS. 2D & F). Overall it appears that the use of IvySS compared with OmpASS and YceISS offers tighter control of dAb formation prior to induction.

Example 3

An amino acid sequence alignment between OmpASS, YceISS and IvySS (FIG. 3A) and evaluation of their codon adaptation index (CAI) (FIG. 3B & Table 3) identified a cassette of eight amino acids (Ivy'SS) at the N-terminus of IvySS that was significantly different from OmpASS and YceISS in terms of amino acid sequence, but also contained a large proportion of rare codons (Table 3).

Figure 3:
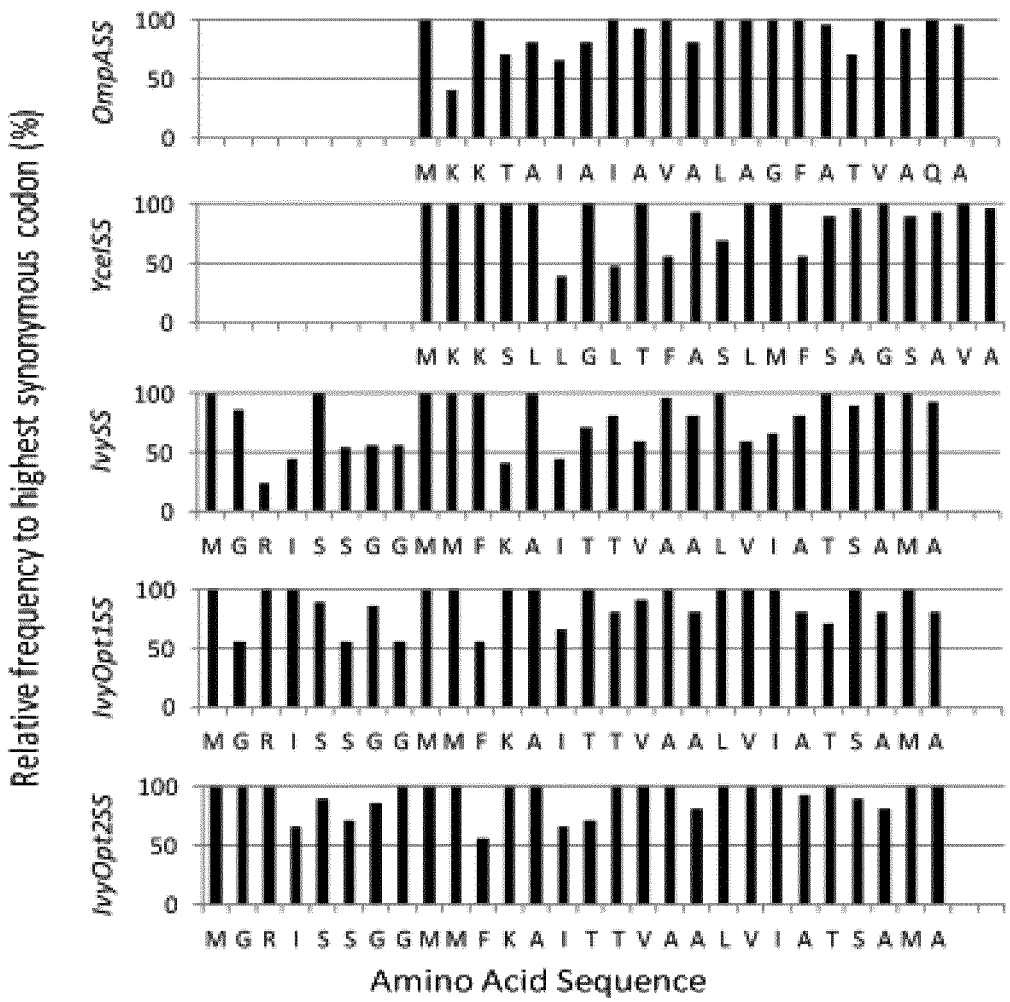
FIG. 3. Signal sequences amino acid sequence alignments and evaluation of their codon adaptation indices. (A) Amino acid sequence alignments for YceISS (SEQ ID NO: 35) and IvySS (SEQ ID NO: 34) are referenced against the OmpASS (SEQ ID NO: 33). (B) Adaptiveness of each codon position was calculated as a ratio of that codon frequency against the most abundant synonymous codon with reference to the *E. coli* codon usage table derived from the Kazusa *E. coli* codon usage database. Amino acid sequences in 'B ' are aligned from the first methionine after the Ivy'SS cassette.

FIG. 3 shows signal sequences amino acid sequence alignments and evaluation of their codon adaptation indices. (A) Amino acid sequence alignments for YceISS (SEQ ID NO: 35) and IvySS (SEQ ID NO: 34) are referenced against the OmpASS (SEQ ID NO: 33). Conserved amino acids are highlighted. (B) Adaptiveness of each codon position was calculated as a ratio of that codon frequency against the most abundant synonymous codon with reference to the *E. coli* codon usage table derived from the Kazusa *E. coli* codon usage database. Amino acid sequences in 'B' are aligned from the first methionine after the Ivy'SS cassette.

It was hypothesized that the presence of this eight-codon cassette or the resulting amino acids for IvySS might affect the level and the rate of dAb expression before induction (i.e. the basal level). To investigate the impact of the identified Ivy'SS cassette in facilitating dAb formation during high cell density fed-batch fermentation, two modified signal sequences were developed; IvyTruncSS, a signal sequence based on that for IvySS with Ivy'SS removed; and also Ivy'OmpASS, which is the product of the fusion of the codons for Ivy'SS to the N-terminus of OmpASS. Additionally, two codon optimised IvySS signal sequences, IvyOpt1SS and IvyOpt2SS, were created (FIG. 3B, and Materials and Methods for details) to explore if the rate of expression of the dAb can be increased without changing the basal dAb expression level and the broth viscosity. The resultant CAI values for the four modified Ivy related signal sequences are given in Table 4.

Example 4

Figure 4:
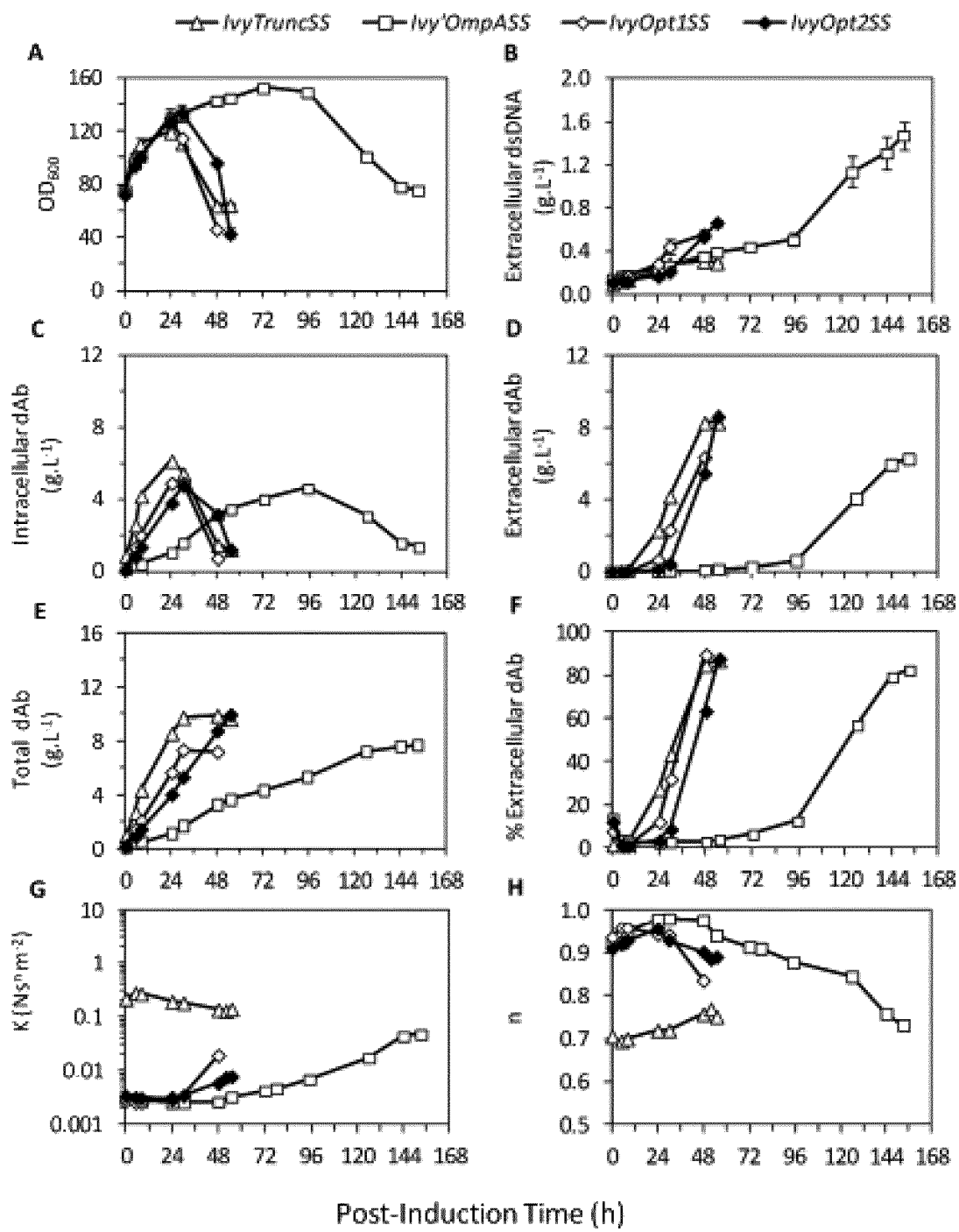
FIG. 4. Post-induction fermentation profiles for high cell density E. coli W3110 fed-batch cultures. N-terminal signal sequence and basal (pre-induction) expression level: (Δ), IvyTruncSS, 0.90 g·L$^{-1}$, (□), Ivy'OmpASS, 0.086 g·L$^{-1}$, (◇), IvyOpt1SS, 0.16 g·L$^{-1}$ and (♦), IvyOpt2SS, 0.089 g·L$^{-1}$. See FIG. 2 for details. Results were taken from single fermentation samples (m=3).

The growth of *E. coli* W3110 cultures expressing dAb with the modified signal sequence is described in FIG. 4. All the modified signal sequences presented in FIG. 4 were efficiently cleaved resulting in a correctly folded dAb molecule.

FIG. 4 shows post-induction fermentation profiles for high cell density *E. coli* W3110 fed-batch cultures. N-terminal signal sequence and basal (pre-induction) expression level: (Δ), IvyTruncSS, 0.90 g·L$^{-1}$, (☐), Ivy'OmpASS, 0.086 g·L$^{-1}$, (◇), IvyOpt1SS, 0.16 g·L$^{-1}$ and (♦), IvyOpt2SS, 0.089 g·L$^{-1}$. See FIG. 2 for details. Results were taken from single fermentation samples (m=3).

TABLE 7

| Signal sequence | dAb pre-induction basal expression, g · L$^{-1}$ (+/−sd or range) |
|---|---|
| IvyTruncSS | 0.90 ± 0.09 |
| Ivy'OmpASS | 0.086 ± 0.008 |
| IvyOpt1SS | 0.16 ± 0.01 |
| IvyOpt2SS | 0.089 ± 0.008 |

The use of the IvyTruncSS resulted in earlier cessation of growth, greater dsDNA release and lower dAb formation than observed for the use of IvySS (FIG. 2). The level of basal expression of the dAb at the time of induction is higher than for the use of IvySS and the viscosity of the both just prior to and after induction is significantly higher. Hence the presence of Ivy'SS appears to be critical to reducing the early expression prior to induction and hence the resultant high viscosity levels (FIG. 4G). The increased rate of expression observed (FIG. 4E) is consistent with the removal of a sequence containing a large proportion of rare codons. The use of the Ivy'OmpASS resulted in growth, dsDNA release, dAb formation and location and viscosity profiles similar to those observed when using the IvySS (FIG. 2) confirming the importance of Ivy'SS in reducing basal dAb expression. Again a low viscosity is observed for Ivy'OmpASS at the start of the induction phase and the subsequent viscosity rise is attributed to the presence of extracellular dsDNA. Similarly, as with IvySS, extended fermentation times were needed to yield significant expression levels of dAb and release to the extracellular environment. The use of IvyOpt1SS and IvyOpt2SS resulted in low basal expression of the dAb at the point of induction (FIG. 4 legend). The result is a low viscosity broth (FIG. 4G). As expected, the reduced incidence of rare codons in the optimised signal sequences leads to an increased rate of dAb formation (FIG. 4E). Again, as with the use of IvySS, the rise in viscosity of the broth post-induction is attributable to dsDNA release. IvyOpt2SS appears to yield a lower basal expression, a higher dAb titre and a lower viscosity broth than for IvyOpt1SS.

Example 5

Figure 5:
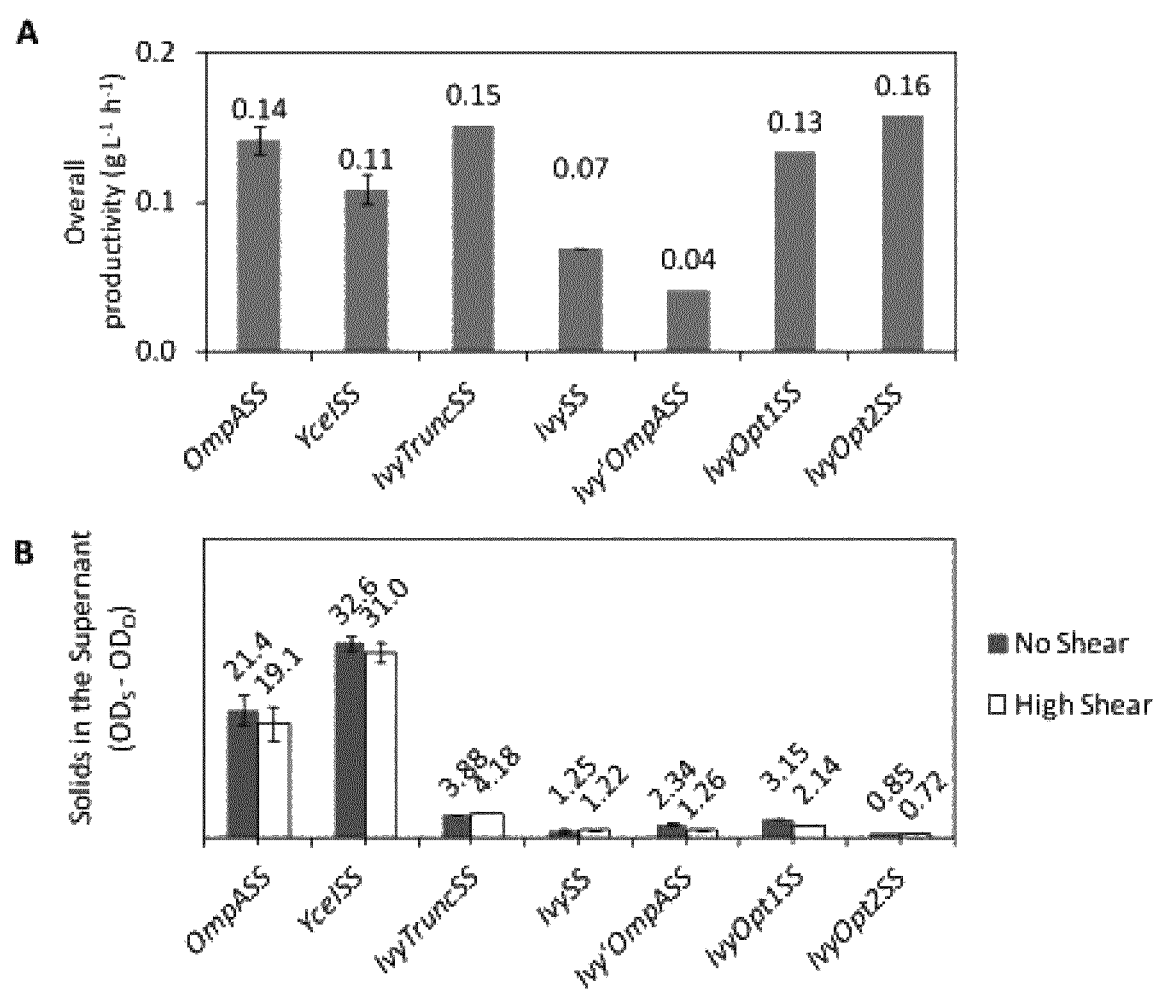
FIG. 5. (A) Overall productivity calculated as the mass of extracellular dAb, per litre of broth per total post-induction time (B) centrifugation performance of E. coli harvest cultures expressing a dAb with different N-terminal signal sequences; OmpASS (48 h post-induction), YceISS (48 h), IvyTruncSS (55 h), Ivy'OmpA (153 h) and Ivy codon optimised signal sequences IvyOpt1 (48 h) and IvyOpt2 (55 h). Cell broths were exposed to conditions of: (■), no shear; (□), high shear stress (maximum energy dissipation rate (ε) of 0.53×10$^6$ W·kg$^{-1}$ for 20 s), and then processed by USD centrifugation (V=2.0 mL, t=420 s, Σ=0.164 m$^2$, (see text), V/tΣ=2.9×10$^{-8}$ m·s$^{-1}$). Results were taken from replicated fermenters (n=3) for OmpASS and YceISS or single fermenter samples for remaining signal sequences. Sample characterization for (B) was in triplicate (m=3). Results shown as mean+/−SD.

The fermenter productivity as measured for the total titre post-induction, is compared in FIG. 5A for the range of signal sequences studied. The low values of dAb for strains using IvySS and Ivy'OmpASS are evidently due to the extended times (~150 h) needed for product formation and release. Strains using IvyOpt1SS, IvyOpt2SS and IvyTruncSS all yield maximum dAb concentration within 24 h of induction and high fermenter productivity levels. Mass spectrometry analysis (not shown here) suggested the signal sequence was completely removed from the dAb for all of the constructs studied in FIG. 5. The clarification of the final broths using USD centrifugation is summarised in FIG. 5B. The conditions used are representative of industrial scale disc stack or solid bowl continuous flow centrifuges operating at low end of this flow rate capacity and fitted with a high shear stress feed zone. A no shear stress feed, as for a bench top centrifuge, is mimicked as a comparative control.

FIG. 5 (A) shows overall productivity calculated as the mass of extracellular dAb, per litre of broth per total post-induction time; and (B) shows centrifugation performance of E. coli harvest cultures expressing a dAb with different N-terminal signal sequences; OmpASS (48 h post-induction), YceISS (48 h), IvyTruncSS (55 h), Ivy'OmpA (153 h) and Ivy codon optimised signal sequences IvyOpt1 (48 h) and IvyOpt2 (55 h). Cell broths were exposed to conditions of: (■) no shear; (□), high shear stress (maximum energy dissipation rate ($\varepsilon$) of $0.53 \times 10^6$ W·kg$^{-1}$ for 20 s), and then processed by USD centrifugation (V=2.0 mL, t=420 s, $\Sigma$=0.164 m$^2$, (see text), V/t$\Sigma$=2.9×10$^{-8}$ m·s$^{-1}$,). Results were taken from replicated fermenters (n=3) for OmpASS and YceISS or single fermenter samples for remaining signal sequences. Sample characterization for (B) was in triplicate (m=3). Results shown as mean+/−SD.

The high viscosities of the broths obtained using OmpASS and YceISS resulted in a poorly clarified supernatant with ~50% and ~80% of solids still in the supernatant respectively. The remaining broths are all clarified to >10 fold greater extent (~1-4% remaining solids) so that the differences in performance are less obvious. The medium viscosity broth obtained when using the IvyTruncSS (FIG. 4G) resulted in a clarified broth at the high end of this range (~4%). The remaining broths were all clarified to a greater extent reflecting the even lower viscosities of the final broths. In nearly all cases, the effect of high shear stress resulted in 5-30% improvement in clarification indicating a probable reduction of viscosity e.g. due to break up of fluid structures (such as polymer bridges). Several strains result in both high fermenter productivity and good centrifugal clarification. Strains using IvyOpt2SS followed by IvyOpt1SS provide the most promising choices based on this study. The use of IvyTruncSS also does perform well, but the indication is that clarification by centrifugation is more challenging.

Summary of Examples

Two signal sequences, IvySS and YceISS have been identified, which enable the secretion of a heterologous protein in E. coli periplasmic space. A strain using YceISS was shown to perform in a 1 L fed-batch, stirred-tank fermenter in a comparable way with the use of OmpASS (FIG. 2). The use of the IvySS resulted in considerably lower broth viscosities compared to those obtained with the use of OmpASS and YceISS albeit with slower production rates (FIG. 2 & Table 3) and lower overall productivities (FIG. 5A). We discuss firstly the reason for the formation of high viscosity broths with the media and fermentation strategy used here and secondly the development of signal sequences based on IvySS.

The initial studies using OmpASS, YceISS and IvySS suggest that a high basal (i.e. pre-induction) expression of dAb results in the formation of a highly viscous fermentation broth at the start of induction (FIG. 2). Such high viscosities are continued throughout the remainder of the fermentation with any further increase probably attributable to DNA release with increased cell autolysis. This relationship between basal expression and viscosity is supported by observations using a range of other signal sequences (FIG. 4) and is summarised in Table 5. Preliminary studies, not shown here, demonstrated a high viscosity broth (K~1.1 Ns$^n$m$^{-2}$) for IvySS when induction was carried out during rather than after the end of the exponential growth phase mimicking a high basal expression.

The high viscosities observed by the time of induction can probably be attributed to formation of extracellular polymeric substances (EPS) during fermentation, these being a key component of microbial biofilms. Factors such as growth phase, media composition, temperature, oxygen limitation, nitrogen and cation deficiency have been shown to control EPS biosynthesis. For other microbial systems, exponential growth itself has been linked to the formation of EPS and biofilm. Acetate has also been linked to EPS formation. Biofilm and EPS formation in general has been shown to lead to reduction of growth rate. Observations in this study suggest it is possible that the expression of dAb combined with the effect of environmental conditions pre-induction might promote EPS formation.

For the fermentations studied here the control strategies for the DO are such that oxygen limitation (DO~0%), causing hypoxic conditions, occurs in the exponential growth phase before induction. Both hypoxia and exponential growth are linked to formation of fermentative metabolism by-products and overflow metabolism products respectively, such as acetate. Such conditions, combined with the presence of high basal levels of dAb are possibly leading to EPS formation. Subsequent to induction, the conditions are such that any acetate formed is likely to have been consumed before the start of the nutrient feed. From this point on, the controlled constant nutrient feed rate will mean that cells are in a linear or stationary phase of growth and the DO control is efficiently maintained at 30%; i.e. there is unlikely to be any significant levels of acetate formation present and hence no further EPS formation despite the high levels of dAb. Hence, the control of fermentation conditions prior to induction may be used to avoid acetate formation. Alternatively, media adjustment can diminish biofilm formation e.g. reduced presence of soy or the use of glucose rather than glycerol (as used in this work) as a carbon source. In this study, the fermentations were carried out using a soytone containing medium; the disadvantages of a high viscosity broth when using OmpASS to produce the same dAb have been overcome through the use of soy-free fermentation media. Basal expression (and hence for the system studied here, EPS formation) might be reduced by use of a more tightly controlled expression system but this may generate other process related challenges. Another potential route to eliminate EPS formation is by the use of a biofilm deficient *E. coli* strain. Future work will seek to confirm the impact of EPS leading to the high viscosities observed in this study. The focus here is on how selected signal sequences may be improved to achieve low viscosity fermentation using the existing media and fermentation operating conditions.

Two aspects of the make-up of IvySS appear to relate to its performance in determining the basal expression and the post-induction productivity of the dAb. Firstly the presence of an eight codon cassette (Ivy'SS) at the start of IvySS leads to tight control of protein expression before induction, i.e. low basal expression. Secondly a low codon adaptation index (CAI) appears to lead to a low rate of expression of the protein. The effect of choice of signal sequence, including modified Ivy signal sequences to retain low basal expression while increasing productivity, is summarized in Table 5. When Ivy'SS was present at the N-terminus of the signal sequence, the level of basal expression prior to induction of dAb expression was low and a broth of low viscosity was obtained. The low basal levels achieved with IvyOpt1SS and IvyOpt2SS (FIG. 4) suggest that it is the amino acid sequence, and not the presence of rare codons in the gene sequence which determines the basal expression level.

The initial productivity is possibly related to the CAI which in turn is linked to the rate of translation elongation and dAb formation. The presence of rare codons at the 5' terminus of mRNA has been hypothesized to lead to slow elongation of the nascent polypeptide during translation to reduced ribosome traffic jams, this leading to lower initial cell productivity. From Table 5, a low CAI to sequence length value led to a low initial productivity e.g. as seen for IvySS and Ivy'OmpASS, while for all other signal sequences there is a high CAI per codon number value leading to high initial productivity. Ideally this analysis should be weighted towards the N terminal end of the construct. This is particularly when rare codons are present for the two strains giving low initial productivity as for the ones using IvySS and Ivy'OmpASS. The increase in the initial productivity of dAb for IvyOpt1SS and IvyOpt2SS compared with that obtained using IvySS could be due to either the modified codon sequence or the removal of rare codons.

IvyOpt2SS is designed by optimisation based on a reference set of optimal codons frequently represented in genes that are highly and continuously expressed during exponential growth while IvyOpt1SS is designed based on expression of all *E. coli* genes. The former leads to higher CAI per codon number (Table 5) and this might lead to the greater overall productivity noted (FIG. 5A). Future work will explore further the potential for such optimisation to further improve the overall expression level while still preventing significant basal expression leading to high viscosity broths.

JOURNAL REFERENCES

Rice P, Longden I, Bleasby A. 2000. EMBOSS: The European Molecular Biology Open Software Suite. Trend Genet 16(6):276-277.

Voulgaris I, Finka G, Uden M, Hoare M. 2015. Enhancing the selective extracellular location of a recombinant *E. coli* domain antibody by management of fermentation conditions. Appl Microbiol Biotechnol 99(20):8441-8453.

Chatel A, Kumpalume P, Hoare M. 2014a. Ultra scale-down characterization of the impact of conditioning methods for harvested cell broths on clarification by continuous centrifugation—Recovery of domain antibodies from rec *E. coli*. Biotechnol Bioeng 111(5):913-924.

Sharp P M, Li W-H. 1987. The codon adaptation index-a measure of directional synonymous codon usage bias, and its potential applications. Nucleic Acids Res 15(3):1281-1295.

```
                             Other Sequences

SEQ ID NO: 53: Amino acid sequence of DOM0101
EVQLLESGGGLVQPGGSLRLSCAASGFTFAHETMVWVRQAPGKGLEWVSH
IPPDGQDPFYADSVKGRFTISRDNSKNTLYLQMNSLRAEDTAVYHCALLP
KRGPWFDYWGQGTLVTVSS SEQ ID NO: 54: DNA sequence of DOM0101-(no signal
sequence)
GAAGTACAACTGCTGGAGAGCGGTGGCGGCCTGGTTCAACCGGGTGGTTC
CCTGCGCCTGTCCTGTGCGGCATCTGGTTTCACCTTCGCACACGAAACCA
TGGTGTGGGTTCGCCAAGCTCCGGGCAAAGGCCTGGAATGGGTAAGCCAC
ATTCCTCCAGATGGCCAGGACCCATTCTATGCGGATTCCGTTAAGGGTCG
CTTTACCATTTCTCGTGATAACTCCAAAAACACCCTGTACCTGCAGATGA
ACTCCCTGCGCGCCGAGGATACTGCGGTGTACCATTGTGCGCTGCTGCCT
AAACGTGGCCCGTGGTTCGATTACTGGGGTCAGGGTACTCTGGTCACCGT
AAGCAGC
```

The invention claimed is:

1. A recombinant signal sequence comprising (a) the sequence MGRISSGG (SEQ ID NO: 1) or a variant thereof that differs in sequence by 1 amino acid substitution, deletion or insertion, and (b) a heterologous signal sequence immediately C-terminal to (a).

2. A recombinant fusion protein comprising (a) the recombinant signal sequence of claim 1; and (b) a heterologous recombinant protein C-terminal to (a).

3. The recombinant signal sequence of claim 1, wherein the signal sequence comprises MGRISSGG (SEQ ID NO: 1).

4. The recombinant signal sequence of claim 1, wherein the signal sequence comprises the variant of MGRISSGG (SEQ ID NO: 1) that differs in sequence by 1 amino acid substitution, deletion or insertion.

5. The recombinant signal sequence of claim 1, wherein the heterologous signal sequence is an *Escherichia coli* signal sequence.

6. The recombinant signal sequence of claim 5, wherein the heterologous signal sequence is a periplasmic signal sequence from *Escherichia coli*.

7. The recombinant signal sequence of claim 5, wherein the heterologous signal sequence is selected from the group consisting of a OmpA signal sequence, a MalE signal sequence, a PelB signal sequence, a OmpT signal sequence, and a LamB signal sequence.

8. The recombinant signal sequence of claim 1, wherein the heterologous signal sequence comprises a sequence selected from the group consisting of SEQ ID NO: 33, SEQ ID NO: 35, SEQ ID NO: 36, SEQ ID NO: 37, SEQ ID NO: 38, SEQ ID NO: 39, and SEQ ID NO: 40.

9. The recombinant signal sequence of claim 8, wherein the heterologous signal sequence comprises SEQ ID NO: 33.

10. The recombinant signal sequence of claim 9, wherein the heterologous signal sequence consists of SEQ ID NO: 33.

11. The recombinant signal sequence of claim 1, wherein the recombinant signal sequence comprises the sequence MGRISSGGMKKTAIAIAVALAGFATVAQA (SEQ ID NO: 55).

12. The recombinant signal sequence of claim 1, wherein the recombinant signal sequence consists of the sequence MGRISSGGMKKTAIAIAVALAGFATVAQA (SEQ ID NO: 55).

13. The recombinant fusion protein of claim 2, wherein the recombinant signal sequence comprises the sequence MGRISSGGMKKTAIAIAVALAGFATVAQA (SEQ ID NO: 55).

14. The recombinant fusion protein of claim 2, wherein the recombinant signal sequence consists of the sequence MGRISSGGMKKTAIAIAVALAGFATVAQA (SEQ ID NO: 55).

15. The recombinant fusion protein of claim 2, wherein the heterologous recombinant protein comprises an antigen binding protein.

16. The recombinant fusion protein of claim 15, wherein the antigen binding protein is selected from the group consisting of a monoclonal antibody, an antibody fragment, and a domain antibody (dAb).

17. The recombinant fusion protein of claim 2, wherein the heterologous recombinant protein comprises a viral protein.

18. The recombinant fusion protein of claim 2, wherein the heterologous recombinant protein comprises a bacterial toxin or a bacterial toxoid.

19. The recombinant fusion protein of claim 2, wherein the heterologous recombinant protein comprises a cancer antigen.

* * * * *